United States Patent
Lambrecht et al.

(10) Patent No.: US 12,426,969 B2
(45) Date of Patent: Sep. 30, 2025

(54) SYSTEMS AND METHODS FOR SELECTING ASSIGNMENTS FOR COMPONENTS OF COMPUTER-ASSISTED DEVICES

(71) Applicant: INTUITIVE SURGICAL OPERATIONS, INC., Sunnyvale, CA (US)

(72) Inventors: Bram Gilbert Antoon Lambrecht, Redwood City, CA (US); John Ryan Steger, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 290 days.

(21) Appl. No.: 18/007,021

(22) PCT Filed: Jul. 27, 2021

(86) PCT No.: PCT/US2021/043323
§ 371 (c)(1),
(2) Date: Jan. 26, 2023

(87) PCT Pub. No.: WO2022/026472
PCT Pub. Date: Feb. 3, 2022

(65) Prior Publication Data
US 2023/0285096 A1    Sep. 14, 2023

Related U.S. Application Data

(60) Provisional application No. 63/057,863, filed on Jul. 28, 2020.

(51) Int. Cl.
A61B 34/30    (2016.01)
A61B 34/00    (2016.01)
(Continued)

(52) U.S. Cl.
CPC .............. *A61B 34/35* (2016.02); *A61B 34/25* (2016.02); *A61B 90/06* (2016.02); *A61B 90/08* (2016.02);
(Continued)

(58) Field of Classification Search
USPC .............................. 700/245–264; 606/1, 130
See application file for complete search history.

(56) References Cited

U.S. PATENT DOCUMENTS 6,311,181 B1    10/2001    Lee et al.
6,331,181 B1    12/2001    Tierney et al.
(Continued)

FOREIGN PATENT DOCUMENTS

WO    WO-2007111737 A2    10/2007
WO    WO-2016201313 A1    12/2016
(Continued)

OTHER PUBLICATIONS

International Search Report and Written Opinion for Application No. PCT/US2021/043324, mailed Feb. 9, 2022, 18 pages.
(Continued)

*Primary Examiner* — Jonathan L Sample
(74) *Attorney, Agent, or Firm* — Artegis Law Group, LLP

(57) ABSTRACT

A device management system can include a device comprising a drive assembly configured to removably couple with an instrument. The drive assembly can include a plurality of drive elements configured to cause movement of the instrument by driving a plurality of input elements of the instrument. A control system can include a processor configured select, for a first drive element of the plurality of drive elements, a first assignment from a plurality of assignments, the first assignment being available to at least two drive elements of the plurality of drive elements. The first assignment can be associated with a first pairing of the first
(Continued)

drive element with a first input element of the plurality of input elements. The processor can be configured to cause the first drive element to adopt the first assignment.

29 Claims, 11 Drawing Sheets

(51) Int. Cl.
*A61B 34/35* (2016.01)
*A61B 90/00* (2016.01)
(52) U.S. Cl.
CPC ... *A61B 2034/254* (2016.02); *A61B 2034/256* (2016.02); *A61B 2034/305* (2016.02); *A61B 2090/066* (2016.02); *A61B 2090/0803* (2016.02)

(56) References Cited

U.S. PATENT DOCUMENTS

| | | | |
|---|---|---|---|
| 6,625,214 B1 | 9/2003 | Umehara et al. | |
| 7,725,214 B2 | 5/2010 | Diolaiti | |
| 7,955,322 B2 | 6/2011 | Devengenzo et al. | |
| 8,529,582 B2 | 9/2013 | Devengenzo et al. | |
| 8,666,544 B2 | 3/2014 | Moll et al. | |
| 8,823,308 B2 | 9/2014 | Nowlin et al. | |
| 10,470,830 B2 | 11/2019 | Hill et al. | |
| 10,786,329 B2 | 9/2020 | Schuh et al. | |
| 11,259,870 B2* | 3/2022 | DiMaio | A61B 34/71 |
| 11,298,186 B2* | 4/2022 | Chou | A61B 34/74 |
| 12,133,702 B2* | 11/2024 | Nowlin | A61B 34/20 |
| 2004/0049205 A1* | 3/2004 | Lee | A61B 34/37 606/130 |
| 2011/0137337 A1* | 6/2011 | van den Dool | A61B 17/29 606/205 |
| 2016/0256154 A1* | 9/2016 | Shelton, IV | A61B 17/105 |
| 2017/0165837 A1* | 6/2017 | Asano | B25J 9/1689 |
| 2018/0001476 A1 | 1/2018 | Tan et al. | |
| 2018/0311005 A1* | 11/2018 | Mccormick | A61B 34/25 |
| 2019/0059985 A1* | 2/2019 | Shelton, IV | A61B 17/07207 |
| 2019/0175294 A1 | 6/2019 | Abbott et al. | |
| 2019/0192245 A1 | 6/2019 | Abbott et al. | |
| 2019/0201102 A1 | 7/2019 | Shelton, IV et al. | |
| 2019/0207911 A1* | 7/2019 | Wiener | G06F 8/65 |
| 2019/0231461 A1 | 8/2019 | Steger et al. | |
| 2020/0045132 A1* | 2/2020 | Kimball | A61B 17/320092 |
| 2020/0146765 A1* | 5/2020 | Hibner | A61B 17/00234 |
| 2020/0170737 A1* | 6/2020 | Bassik | A61B 18/12 |
| 2020/0214776 A1* | 7/2020 | Hingwe | A61B 90/98 |
| 2020/0222129 A1* | 7/2020 | Gomez | G16H 20/40 |
| 2021/0045818 A1* | 2/2021 | Asadian | A61B 34/71 |
| 2021/0169593 A1 | 6/2021 | Kapadia | |
| 2021/0212786 A1 | 7/2021 | Kapadia et al. | |
| 2021/0220063 A1 | 7/2021 | Kapadia et al. | |
| 2021/0338347 A1 | 11/2021 | Kapadia et al. | |
| 2021/0393352 A1 | 12/2021 | Seow et al. | |
| 2022/0039890 A1 | 2/2022 | Waterbury et al. | |
| 2022/0039892 A1 | 2/2022 | Waterbury et al. | |

FOREIGN PATENT DOCUMENTS

| | | |
|---|---|---|
| WO | WO-2017214243 A1 | 12/2017 |
| WO | WO-2018039459 A1 | 3/2018 |
| WO | WO-2018053305 A1 | 3/2018 |
| WO | WO-2018075527 A1 | 4/2018 |
| WO | WO-2018089819 A2 | 5/2018 |
| WO | WO-2019023020 A1 | 1/2019 |
| WO | WO-2019032309 A2 | 2/2019 |
| WO | WO-2019133056 A1 | 7/2019 |
| WO | WO-2019164856 A1 | 8/2019 |
| WO | WO-2022013536 A1 | 1/2022 |

OTHER PUBLICATIONS

International Search Report and Written Opinion for Application No. PCT/US2021/043323, mailed Jan. 31, 2022, 28 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
International Preliminary Report on Patentability for Application No. PCT/US2021/043324 mailed Feb. 9, 2023, 12 pages.
Office Action for Chinese Application No. CN202180030439.7, mailed Apr. 17, 2025, 45 pages.

\* cited by examiner

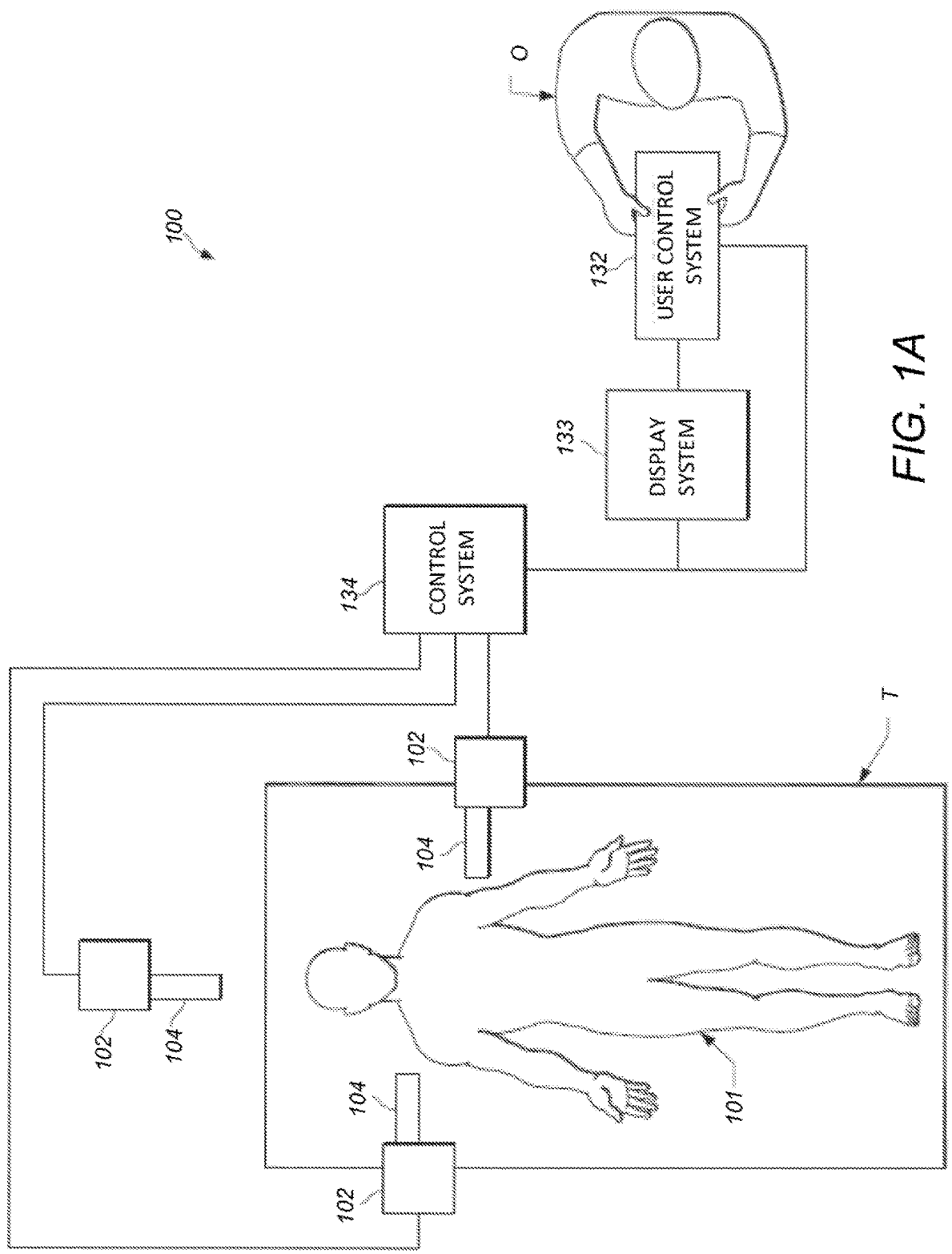

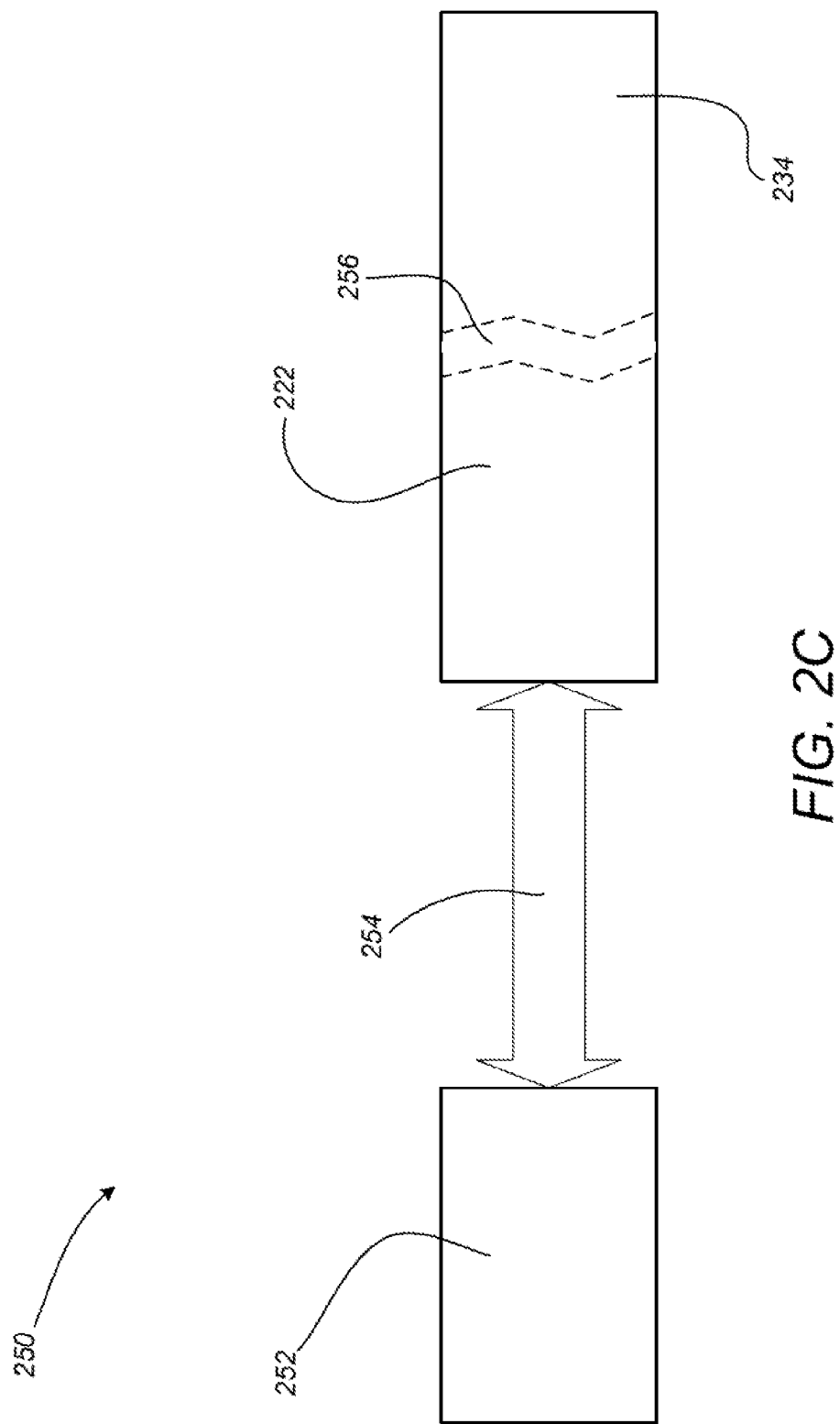

SYSTEMS AND METHODS FOR SELECTING ASSIGNMENTS FOR COMPONENTS OF COMPUTER-ASSISTED DEVICES

CROSS-REFERENCES TO RELATED APPLICATIONS

The present application is a U.S. National Stage patent application of International Patent Application No. PCT/US2021/043323, filed Jul. 27, 2021, the benefit of which is claimed and claims priority to U.S. Provisional Patent Application No. 63/057,863 filed Jul. 28, 2020 and titled "Systems and Methods for Selecting Assignments for Components of Computer-assisted Devices," the disclosure of each of which is incorporated herein by reference in its entirety.

TECHNICAL FIELD

The present technology generally relates to managing devices and, more specifically, to systems and methods for selecting assignments for components of, or drive elements of components of, computer-assisted devices.

BACKGROUND

Computer-assisted devices often comprise modular components that are disposable, reusable, interchangeable, etc. For example, such devices can include manipulator arms having one or more links connected by one or more joints. The arms can be configured to be permanently or releasably mounted at or near a procedure site, such mounted to a ceiling, a wall, a movable cart, an operating table, equipment used for the procedure, etc. In some cases, the arms are interchangeable at a procedure site, and an arm can be positioned at various locations at a procedure site).

As another example of modularity, a computer-assisted device may be removably coupled to various instruments for specific applications and procedures. For example, the computer-assisted device may comprise manipulator arms or other components configured to couple to the instruments. These instruments may also be interchangeable in that an instrument may be configured so that it can couple to different arms or other components of a given computer-assisted device. Use of different instruments can load or wear the arms or other computer-assisted device components, and the subcomponents at comprise those components, in different ways. For example, certain uses or certain instruments may load or wear certain subcomponents more than other subcomponents. Accordingly, there is a need for systems and methods to improve use management of arms and other components of computer-assisted devices.

SUMMARY

In accordance with an embodiment of the present technology, a device management system can include a device comprising a drive assembly. The device may comprise a medical or non-medical device. The drive assembly can be configured to removably couple with an instrument. The drive assembly can include a plurality of drive elements configured to cause movement of the instrument by driving a plurality of input elements of the instrument. The management system can include a control system comprising one or more processors and a memory. The memory can include programmed instructions adapted to cause the one or more processors to perform operations. These operations can include selecting, for a first drive element of the plurality of drive elements, a first assignment from a plurality of assignments, the first assignment being available to at least two drive elements of the plurality of drive elements. The first assignment can be associated with a first pairing of the first drive element with a first input element of the plurality of input elements. The operations can include causing the first drive element to adopt the first assignment.

In accordance with further embodiments of the present technology, a device can include a robotic manipulator and a drive assembly supported by the robotic manipulator. The drive assembly can be configured to removably couple with an instrument. The drive assembly can include a plurality of drive elements configured to cause movement of the instrument by driving a plurality of input elements of the instrument. In a first configuration of the drive assembly, a first drive element of the plurality of drive elements can be positioned to couple with a first input element of the plurality of input elements. In a second configuration of the drive assembly, the first drive element of the plurality of drive elements can be positioned to couple with a second input element of the plurality of input elements.

In accordance with embodiments of the present technology, a method of managing wear on a device comprising a drive assembly configured to removably couple with an instrument can include selecting, for a first drive element of a plurality of drive elements of the drive assembly, a first assignment from a plurality of assignments, the first assignment being available to at least two drive elements of the plurality of drive elements. The method can include causing the first drive element to adopt the first assignment. The first assignment can be associated with a pairing of the first drive element with a first input element of a plurality of input elements of the instrument.

DESCRIPTION OF THE DRAWINGS

Many aspects of the present technology can be better understood with reference to the detailed description along with the following drawings. The components in the drawings are not necessarily drawn to scale. Instead, emphasis is placed on illustrating clearly the principles of the present technology. Furthermore, components can be shown as transparent in certain views for clarity of illustration only and not to indicate that the component is necessarily transparent. Components may also be shown schematically.

FIG. 1A is a schematic illustration of a device configured in accordance with an embodiment of the present technology.

FIG. 2C is a schematic illustration of a drive system of a device configured in accordance with an embodiment of the present technology.

In the specification, it should be appreciated that like reference numerals are used to identify like elements illustrated in one or more of the figures for purposes of illustrating embodiments of the present disclosure and not for purposes of limiting the same.

DETAILED DESCRIPTION

Figure 1B:
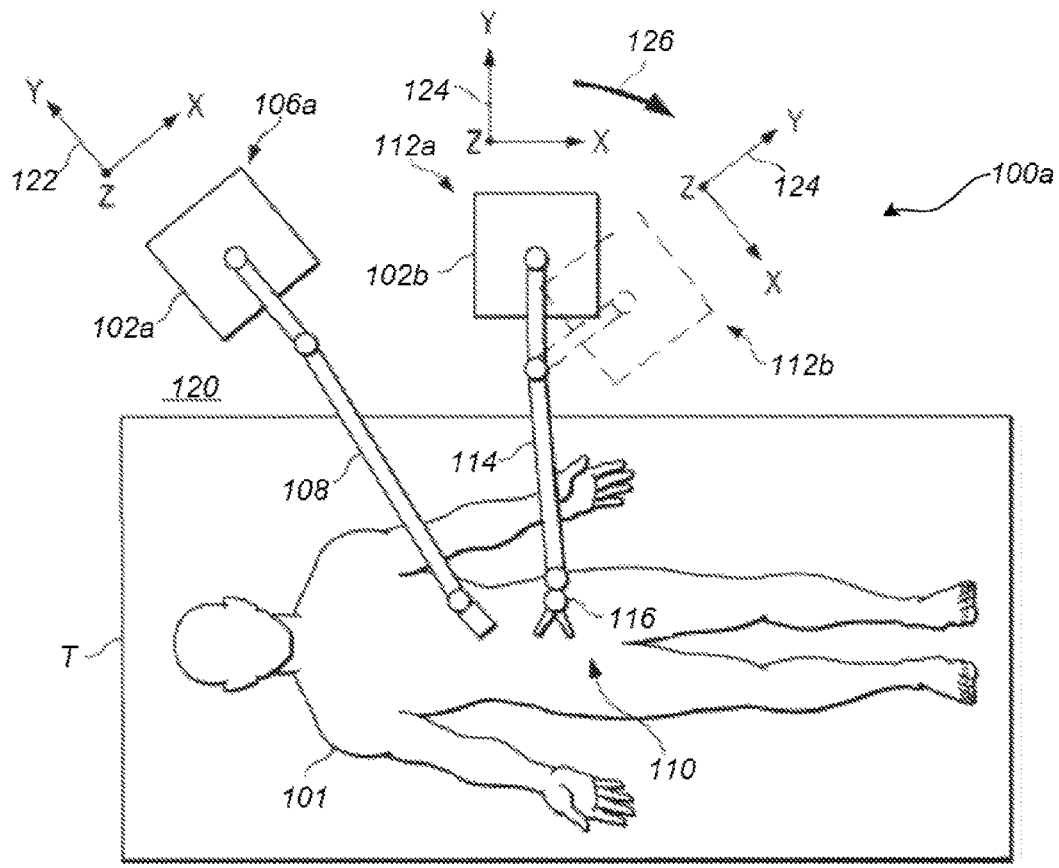
FIG. 1B is a schematic illustration of a device configured in accordance with another embodiment of the present technology, wherein manipulator assemblies of the medical device system are mounted to movable support structure.

Aspects of this disclosure are described in reference to computer-assisted systems and devices, which may include systems and devices that are teleoperated, remote-controlled, autonomous, semiautonomous, robotic, and/or the like. Further, aspects of this disclosure are described in terms of an implementation using a surgical system, such as the da Vinci® Surgical System commercialized by Intuitive Surgical, Inc. of Sunnyvale, California, U.S.A. Knowledgeable persons will understand, however, that inventive aspects disclosed herein may be embodied and implemented in various ways, including robotic and, if applicable, non-robotic embodiments and implementations. Implementations on da Vinci® Surgical Systems are merely examples and are not to be considered as limiting the scope of the inventive aspects disclosed herein. In some embodiments, the instruments, systems, and methods described herein may be suitable for use in, for example, diagnostic, therapeutic, or training procedures regardless of if the procedures are surgical or non-surgical. While some embodiments are provided herein with respect to such procedures, any reference to medical or surgical instruments, or to medical or surgical methods, is intended as non-limiting. Thus, the instruments, systems, and methods described herein may be used for humans, animals, portions of human or animal anatomy, non-surgical diagnosis, as well as for industrial systems, general robotic, or teleoperational systems. As further examples, the instruments, systems, and methods described herein may be used for non-medical purposes including industrial uses, general robotic uses, sensing or manipulating non-tissue work pieces, cosmetic improvements, imaging of human or animal anatomy, gathering data from human or animal anatomy, setting up or taking down systems, training medical or non-medical personnel, and/or the like. Additional example applications include use for procedures on tissue removed from human or animal anatomies (without return to a human or animal anatomy) and for procedures on human or animal cadavers. Further, these techniques can also be used for medical treatment or diagnosis procedures that include, or do not include, surgical aspects.

The present technology generally relates to systems and methods for selecting assignments for components of devices. Such devices can include, for example, computer-assisted medical devices having one or more manipulator arms (or other articulable structures, or other similar or appropriate structures) adapted to be operably coupled to one or more instruments (e.g., non-medical or medical instruments, manipulation instruments such as scissors, or imaging instruments such as cameras, or other apparatuses). The various components of the devices described herein are subject to loading or wear over the course of time and over stages of the same procedure or over multiple procedures. Specific loading and wear can be attributed to many variables. These variables include, but are not limited to, the types of instruments used, the load types realized during procedures, overall component age, orientation of the manipulator assemblies and other components during a given procedure, orientation of the patient during a procedure, cleaning, reprocessing, services and maintenance, repair, and ambient conditions in the procedural and/or storage environments. For example, the type of instrument and/or type of procedure can result in specific types of loading on the components of the manipulator assemblies and/or instruments. Certain types of instruments and procedures can involve higher: frequency of loads, peak or average load magnitudes, load durations, peak or average momentums, peak or average torques or linear forces, ranges of motion, peak or average velocities or acceleration or jerks, numbers of direction reversals, number of actuations, durations of use, amounts of work, instantaneous or average power, peak or average temperatures or temperature ranges, frequency or number of temperature cycles, etc., than other procedures. Also, manipulator or instrument orientation can result in unique distribution of lubricants (e.g., sometime disadvantageous distribution) and/or unique gravity-induced loads on joints and other components. In some cases, the ambient environment can introduce unique wear to the system via humidity levels, temperature levels, ambient pressure (e.g., associated with altitude), and/or particulate (e.g., dust, sand, etc.) levels, and the like.

Types of loading or wear introduced by the above-described variables can include, but are not limited to, abrasion, corrosion, adhesion, thermal fatigue, mechanical fatigue, gouging, galling, fretting, pitting, brinelling, spalling, seizing, cracking (e.g., stress corrosion cracking), rusting, and creep/plastic deformation. The various types of loading or wear attributed to the above-listed variables can cause performance degradation or failures to different specific components, subcomponents comprising those components, and/or other portions of the devices. For example, loading or wear can be applied to drivetrain subcomponents such as actuators (e.g. motors, solenoids), bearings, drive cables, pulleys, gears; joint and link subcomponents. Wear and loading can be attributed to various operations performed by components/subcomponents. Example operations can include instrument movements, staple fires, cuts, ablations, clamps, etc.

In many cases, lower performance or failure of a subcomponent (e.g., of a manipulator arm or instrument) can lead to lower performance or failure of the entire component or larger device. For example, lower performance or failure of a drive assembly subcomponent, a sensor system subcomponent, a control system subcomponent, or some other subcomponent of a manipulator arm can render the entire manipulator arm less capable or unusable without service or repair. Examples of drive assembly subcomponents include drive elements configured to couple with and import motion or motive force (e.g. linear force or rotary torque) to input elements of an instrument, as well as drivetrain subcomponents coupled to drive the drive elements, such as cables, metal bands, drive screws, cable, gears and gear shafts, pulleys, levers, gimbals, actuators such as motors and solenoids, structural subcomponents such as chassis and clevises, and other subcomponents comprising a drivetrain. Increased use of a component or a subcomponent, compared to use of other components or subcomponents, can lead to greater loading, greater wear, lower performance, or earlier failure of that component or subcomponent, as compared to the other components or subcomponents. It is, thus, advantageous to reduce over-use of components or subcomponents, as compared to other components or subcomponents, if such reduction is possible. As used herein, "couple," "coupled," or any form thereof, refer to connections between two or more components, whether directly (e.g., via direct contact) or indirectly (e.g., via one or more intermediate structures).

In order to reduce the variance in loading and wear between the components in the medical devices described herein, and thereby increase the overall performance or life of the device, various methods and systems can be implemented as described herein. These methods and systems include, for example, randomized or pseudorandomized couplings between the drive assemblies and the instruments. In some implementations, the loads and wear of specific components can be monitored in order to assign instruments to less-used components of the device. For example, certain embodiments of the present technology can include devices with drive assemblies configured to couple with instruments. The drive assembly comprises a plurality of drive elements configured to cause movement of the instrument by driving a plurality of input elements of the instrument. The drive elements of a given device (e.g., a medical device) and input elements of a given instrument may be configured to couple with each other in a plurality of orientations or other arrangements. In some instances, the drive elements of a given device are configured to couple with input elements of a variety of different instruments. The systems of the present technology can include one or more processors configured to execute instructions to manage the coupling between the devices and instruments to more evenly distribute loading or wear on the drive elements.

The present disclosure describes various instruments and portions of instruments in terms of their state in three-dimensional space. As used herein, the term "position" refers to the location of an object or a portion of an object in a three-dimensional space (e.g., three degrees of translational freedom along Cartesian X, Y, and Z coordinates). As used herein, the term "orientation" refers to the rotational placement of an object or a portion of an object (e.g., three degrees of rotational freedom, such as roll, pitch, and yaw). As used herein, the term "pose" refers to the position of an object or a portion of an object in at least one degree of translational freedom and to the orientation of that object or portion of the object in at least one degree of rotational freedom (e.g., up to six total degrees of freedom).

FIG. 1A is a simplified diagram of a device in accordance with an embodiment of the present technology. Specifically, FIG. 1A illustrates a computer-assisted medical device 100. In some embodiments, the device 100 may be suitable for use in, for example, diagnostic, therapeutic, training, or other procedures regardless of if the procedures are surgical or non-surgical. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic, general teleoperational, or robotic medical systems.

As shown in FIG. 1A, the device 100 can include one or more manipulator assemblies 102. Although three manipulator assemblies 102 are illustrated in the embodiment of FIG. 1A, in other embodiments, more or fewer manipulator assemblies may be used. The exact number of manipulator assemblies will depend on the procedure and the space constraints within the operating room, among other factors. Each manipulator assembly 102 may comprise one or more manipulator arms (e.g., robotic manipulator arms). Multiple user control systems 132 may be co-located, or they may be positioned in separate locations. Multiple user control systems 132 can allow more than one operator to control one or more teleoperated manipulator assemblies in various combinations.

In this medical example, the manipulator assembly 102 is used to operate a medical instrument 104 (e.g., a manipulation, imaging, or other instrument) in performing various procedures on a patient 101. In some embodiments, one or more of the manipulator assemblies 102 includes more than one manipulator arm, and each manipulator arm is configured to have one or more medical instruments 104 mounted thereon. The instrument(s) 104 may be releasably or fixedly mounted to the manipulator assemblies. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. The manipulator assembly 102 may be configured to position and move the medical instrument 104 such that a distal portion of the manipulator assembly 102 and/or the medical instrument 104 pivots about a remote center of motion coincident with the instrument 104's entry aperture into the patient 101. The manipulator assembly 102 may then manipulate the instrument 104 to translate or rotate the instrument 104 in space, such as pivot the instrument 104 about the remote center of motion, insert or retract the instrument 104, and/or roll the instrument 104 about its shaft axis.

In some embodiments, the manipulator assembly 102 may be mounted to or near an operating or surgical table T. In such embodiments, the manipulator assembly 102 may be mounted directly to the table T or to a rail coupled to the table T. In various other embodiments, the manipulator assembly 102 may be mounted to a fixed or movable manipulating system (e.g., mounted to the floor, wall, or ceiling, or to a cart). The manipulating system may be separate from and spaced from the table T in the operating room. In such embodiments, the manipulating system may be independently movable relative to the table T. In such embodiments, one or more of the manipulator assemblies 102 may be mounted to any structure or in any manner as described above. For example, one manipulator assembly 102 may be mounted to the table T and another manipulator assembly 102 may be mounted to a manipulating system. In other examples, an additional manipulator assembly 102 may be mounted to the ceiling of the operating room.

Figure 1C:
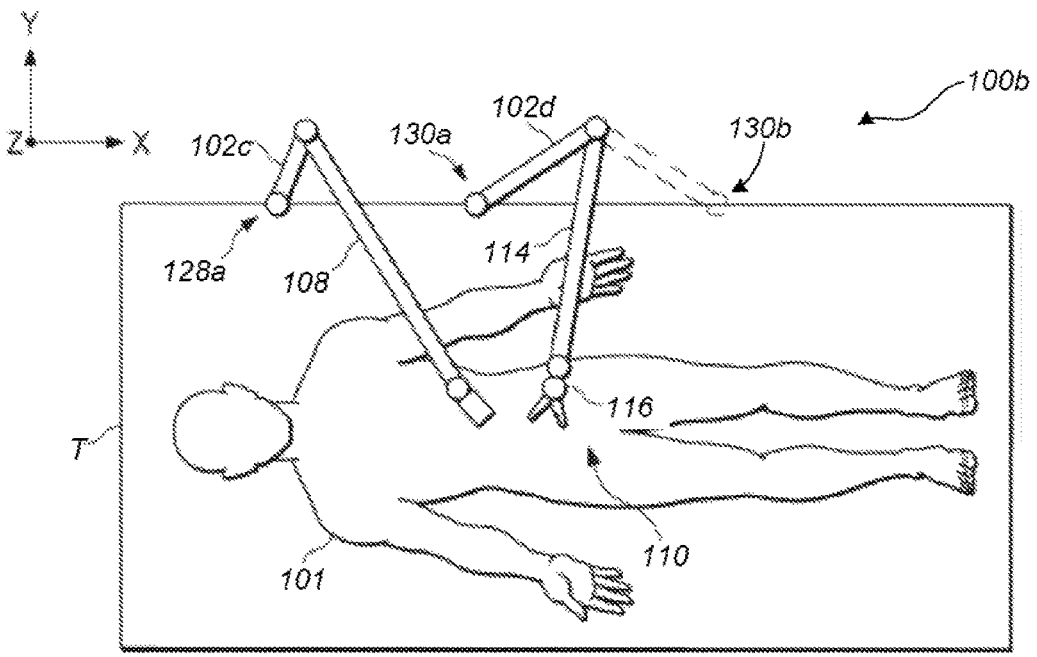
FIG. 1C is a schematic illustration of a device configured in accordance with another embodiment of the present technology, wherein manipulator assemblies of the medical device systems are mounted to a table.

FIGS. 1B and 1C illustrate two such example manipulator assembly configurations. More specifically, FIG. 1B is a schematic plan view of a medical device 100a, showing a patient and two patient-side units that illustrates an example situation in which separate instrument support structures are used during a medical procedure. The medical device 100a can share many or all of the characteristics of the medical device 100 described herein. The patient 101 is shown on an operating table T. An illustrative support structure 102a is shown as a mobile unit that can be moved across the operating room floor. The support structure 102a (e.g., a manipulator assembly) can support an instrument 108 such as an instrument comprising an endoscopic camera, which in the pose shown in FIG. 1B has a field of view (FOV) directed toward a work site 110 (e.g., a medical site such as a surgical site) within the patient 101. An illustrative support structure 102b (e.g., a manipulator assembly) is included, also shown as a mobile unit that can be moved across the operating room floor. The support structure 102b can support an instrument 114, such as a manipulation instrument posed to locate its end effector 116 at the work site 110. In various embodiments, each of the support structures 102a, 102b can replaced by one or multiple support structures. Further, each support structure (e.g. 102a, 102b) can be configured to support one or multiple instruments. The description that follows about the support structures 102a and 102b also applies to the various other support structures each may represent.

As shown in FIG. 1B, the support structure 102a is at a pose 106a relative to a world reference frame 120. The support structure reference frame 122 is associated with an individual link of the support structure's kinematic chain (e.g., a link of a setup structure, a manipulator, or a link of the instrument of support structure 102a) The support structure reference frame 122 orientation changes as the orientation of the associated individual link changes.

As shown in FIG. 1B, the support structure 102b is at a first pose 112a with relative to the world reference frame 120. A support structure reference frame 124 is associated with an individual link of the support structure's kinematic chain. FIG. 1B further shows the support structure 102b at a second dotted-line pose 112b with reference to the world reference frame 120, which illustrates that the support structures 102a, 102b may be placed at and moved to various positions and orientations for and during operation. The reference frame 124 translates and rotates as its associated link translates and rotates, as shown by arrow 126.

FIG. 1C is another schematic plan view illustrating another example medical device configuration. In FIG. 1C, the support structures 102c, 102d of the medical device are mounted to the table T. For example, the support structures 102c, 102d may be mounted at various positions along the table's top or side rail(s) or mounted to a base of the table. The support structure 102c (showing holding a camera instrument 108) is mounted to the table T at a base position 128a. The support structure 102d (shown holding a manipulation instrument 114) is mounted to the table T at a base position 130a. FIG. 1C also illustrates via dotted lines the support structure 102d mounted to the table T at a base position 130b. This is to illustrate that the support structure 102c, 102d may be placed at or moved to various positions and orientations for and during operation.

Returning back to FIG. 1A, the device 100 can include a display system 133 for displaying an image or representation (e.g., a real-time image captured by an imaging instrument, a model derived from sensor data) of the work site and medical instrument 104. The display system 133 and the user control system 132 may be oriented so that an operator O (e.g., a surgeon or other clinician, as illustrated in FIG. 1A) can control the medical instrument 104 and the user control system 132 with the perception of telepresence. The image may be, for example, a two- or three-dimensional image captured by an imaging device of the work site. In some examples, the display system 133 may present images of the work site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including, e.g., time-based or velocity-based information) images and/or as images from models created from the pre-operative or intra-operative image data sets.

The device 100 may also include control system 134. The control system 134 includes at least one memory and at least one computer processor (not shown) for effecting control between the medical instrument 104, the user control system 132, and the display system 133. The control system 134 also includes programmed instructions (e.g., a non-transitory machine-readable medium storing the instructions) to implement some or all the methods described in accordance with aspects disclosed herein, including instructions for providing information to display system 133. While the control system 134 is shown as a single block in the simplified schematic of FIG. 1A, the system may include one, two, or more data processing circuits with one portion of the processing optionally being performed on or adjacent to manipulator assembly 102, another portion of the processing being performed at user control system 132, and/or the like. Any of a wide variety of centralized or distributed data processing architectures may be employed. Similarly, the programmed instructions may be implemented as a number of separate programs or subroutines, or they may be integrated into a number of other aspects of the systems described herein. In one embodiment, the control system 134 supports wireless communication protocols such as Bluetooth, IrDA, HomeRF, IEEE 802.11, DECT, and Wireless Telemetry.

As mentioned above, the user control system 132 can allow the operator O to view the work site and to control the manipulator assembly 102. In some examples, the user control system 132 comprises an operator console, such as located in the same room as the table T. However, it is to be understood that the user control system 132 and operator O can be in a different room or a completely different building from the patient 101. The user control system 132 generally includes one or more input devices for controlling the manipulator assembly 102. The input devices may include any number of a variety of devices, such as joysticks, trackballs, data gloves, trigger-guns, hand-operated controllers, voice recognition devices, body motion or presence sensors, and/or the like. In some embodiments, the input devices are provided with the same degrees of freedom as the associated medical instrument 104. In some embodiments, the input devices may have more or fewer degrees of freedom than the associated the medical instrument 104. In some embodiments, the input devices may optionally be manual input devices which move with six degrees of freedom, and which may also include an actuatable handle for actuating instruments (for example, for closing grasping jaws, applying an electrical potential to an electrode, delivering a therapeutic treatment, and/or the like).

The manipulator assembly 102 supports the medical instrument 104 and may include a kinematic structure comprising any number of joints and links. For example, depending upon the design of the kinematic structure, each of the joints of the kinematic structure may be a non-actuated joint or an actuated joint. In some examples, a non-actuated joint may not include any actuators, or may include only actuator(s) with insufficient motive power to move the associated joint, and therefore is not capable of causing motion of the joint via teleoperation and/or motion control commands from a control system. In some examples, the non-actuated joint may include a brake that permits the control system to prevent and/or restrict motion in the non-actuated joint. In some examples, an actuated joint may include one or more actuators that may control motion of the actuated joint and may be commanded to move the joint teleoperatively and/or carry out other motion commands. In some examples, an actuated joint may further include a brake. In such examples, the brake may be employed in an actuated joint to hold a current pose of the non-actuated joint rather than to actively control motion of the actuated joint.

Figure 2A:
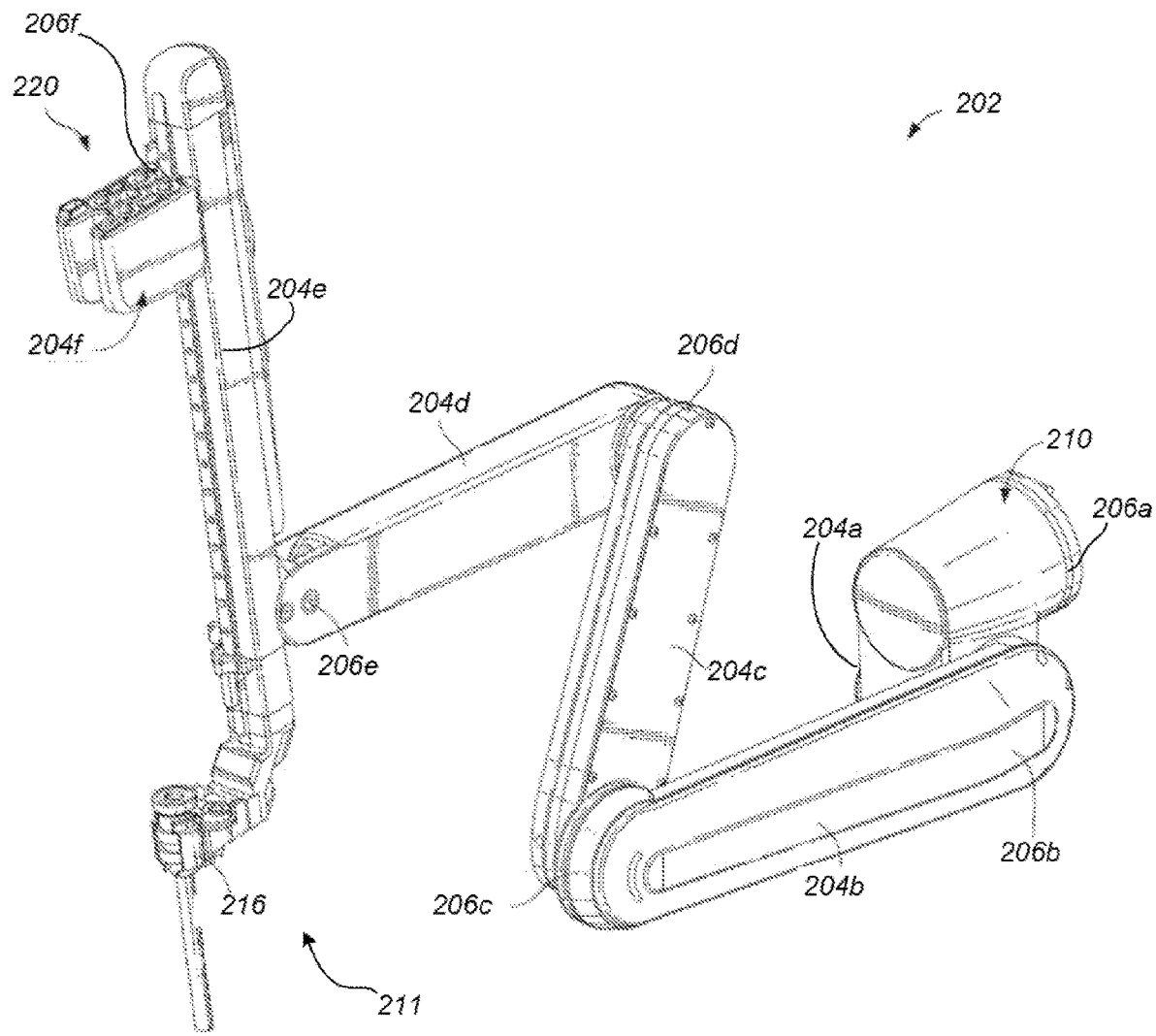
FIG. 2A is an illustration of a manipulator assembly configured in accordance with an embodiment of the present technology.

FIG. 2A, for example, illustrates a manipulator arm 202 configured in accordance with embodiments of the present technology. The manipulator arm 202 can share many or all of the functional and structural characteristics of the other manipulator arms (e.g., a manipulator arm of manipulator assembly 102) described herein. As illustrated, the manipulator arm 202 can include a plurality of links 204a-f (collectively, "204") connected together and to a proximal structure (not shown) by a plurality of joints 206a-f (collectively, "206"). The manipulator arm 202 can be configured to support an instrument (not shown). One or more the joints 206 maybe non-actuated or actuated. In some applications, one or more of the joints 206 are passive and/or configured to resist or prevent unintentional movement of one or more of the links 204 during operation. For example, one or more of the joints 206 can be configured to switch between locked and unlocked configurations.

The manipulator arm 202 can include a mounting structure 210 configured to releasably or fixedly connect the manipulator arm 202 to a mounting site (e.g., a fixed or moveable base, table, ceiling, wall, rollable cart, or any other mounting site described herein). The mounting structure 210 can comprise a joint. For example, in some embodiments, the mounting structure 210 comprises a rotational joint that permits rotational movement of the manipulator arm 202 relative to the mounting site.

The manipulator arm 202 can include an instrument interface 211 configured to releasably receive and connect to one or more instruments. In the example shown in FIG. 2A, the instrument interface 211 is disposed on the links 204e and 204f, and in other embodiments the instrument interface 211 may be located elsewhere. The instrument interface 211 can include a drive assembly 220 configured to interface with an input assembly of an instrument. In some embodiments, the instrument interface 211 includes one or more alignment features configured to orient an instrument when the instrument is connected to the instrument interface 211. For example, the alignment features can include a groove 216 configured to receive a portion of a shaft of the instrument.

Figure 2B:
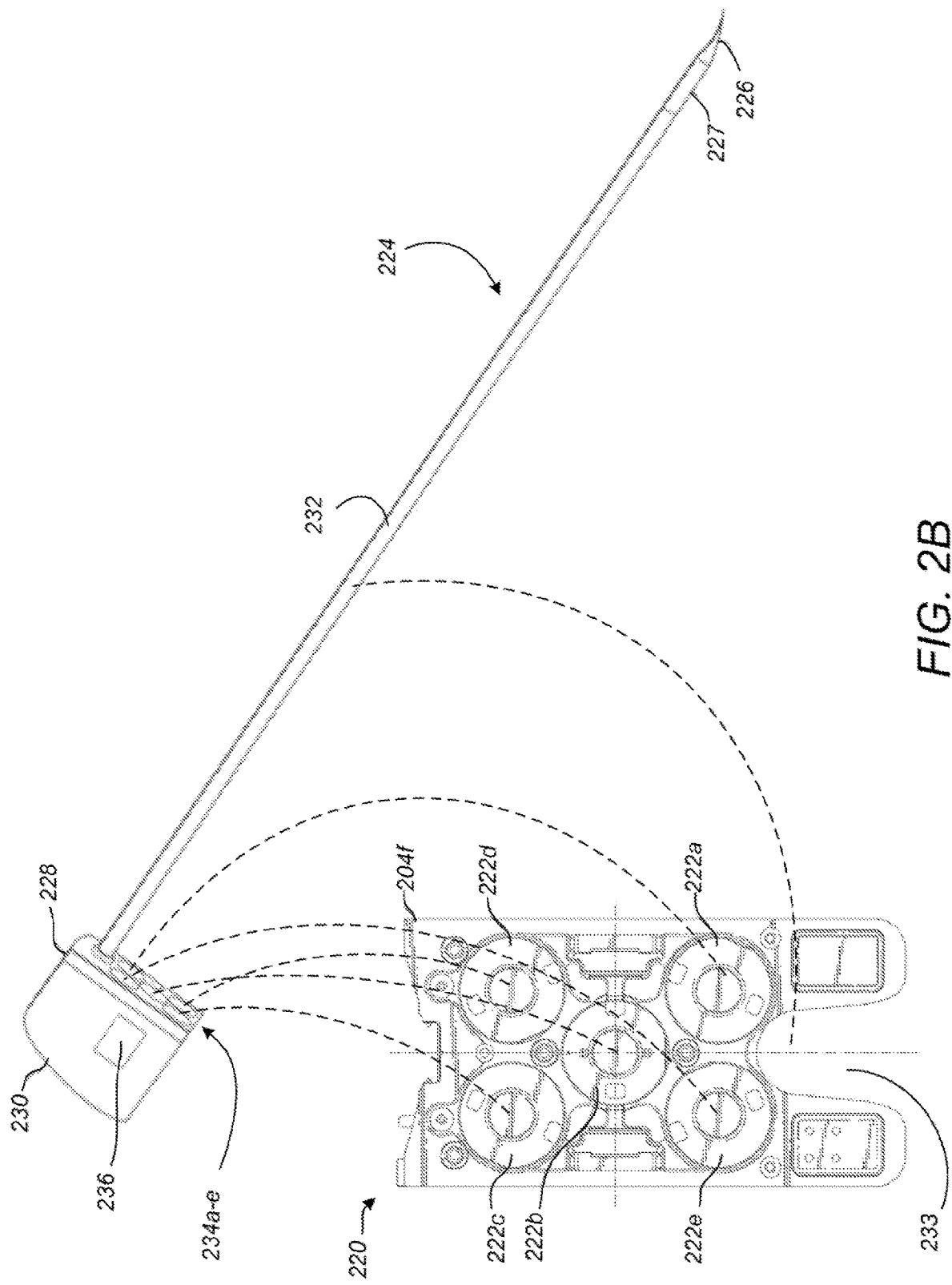
FIG. 2B is an illustration of a drive assembly and an instrument configured for use with of the manipulator assembly of FIG. 2A.

FIG. 2B is an illustration of a portion of the drive assembly 220 and an instrument 224 configured in accordance with embodiments of the present technology. The drive assembly 220 can include one or more drive elements 222 (five are shown as drive elements 222a-e). The drive elements 222 can be mounted onto/into the link 204f (e.g., a carriage). The drive assembly 220 or some other portion of the manipulator arm 202 can include one or more actuators or motors configured to operate the drive elements 222. In some configurations, each of the separate drive elements 222 is driven by a separate motor/actuator. In other configurations, two or more of the drive elements 222 are driven by a shared motor/actuator. As illustrated in FIG. 2B, the drive elements 222 can be rotary discs or other rotary drive elements. In other embodiments, however, one or more of the drive elements 222 can comprise one or more tabs, protrusions, indentations, or other structures, and be configured to impart any combination of rotary or linear motion onto another structure.

The instrument 224 as shown includes a distal end effector 226, a wrist 227 comprising one or more joints, a proximal end chassis 228, a housing 230 over the chassis 228, and a shaft 232 between the end effector 226 and the chassis 228. In various embodiments, the instrument 224 may have fewer or more than these subcomponents, or different instances of these subcomponents. For example, in some embodiments, the instrument 224 lacks the wrist 227 or comprises a wrist 227 with different degrees or freedom or range of motion, lacks the chassis 228, and/or lacks the housing 230. As another example, in some embodiments, the chassis 228 and the housing 230 are combined into a single component. The shaft 232 can be configured (e.g., sized and shaped) to fit at least partially within an indentation or channel 233 in the link 204f. The end effector 226 is coupled to the shaft 232 with or without one or more intervening joints, such as the wrist 227. Various wrist 227 architectures allow the orientation of the end effector 226 to change with reference to the shaft 232 in various combinations of pitch, yaw, and/or roll. Optionally, the end effector roll function is carried out by rolling the shaft 232 or the chassis 228. Various drivetrain subcomponents and mechanisms are mounted on the chassis 228 and function to receive either mechanical or electrical inputs from the manipulator associated with the instrument 224. These inputs can be used to orient and operate the end effector 226. Example drivetrain subcomponents are listed earlier in this application.

Referring to FIG. 2B, the chassis 228 will typically include one or more input elements 234 (five are shown as input elements 234a-e) adapted for coupling to drive elements 222 of the manipulator arm 202 (e.g., of the drive assembly of the manipulator arm 202), as indicated by the broken lines connecting respective drive elements 222 to respective input elements 234. Coupling between the drive elements 222 and the input elements 234 can be direct (e.g., with direct contact between the drive elements 222 and the input elements 234) or indirect through one or more intermediate structures. For example, in some applications, an adapter is positioned between the input elements 234 and the drive elements 222. The adapter can include one or more transmission elements (e.g., discs, compliant protrusions or indentations) configured to allow or facilitate the transmission of linear or rotary force (torque), motion, and/or other inputs from the drive elements 222 to the input elements 234. In a medical example, the adapter can be a sterile adapter configured to inhibit or prevent transmission of pathogens from the drive assembly to the instrument 224 (and thereby to a patient). The drive elements 222 drive the input elements 234 on the instrument 224 (or another instrument, such as instrument 104) in response to commands from the control system (e.g., a control system 134, see FIG. 1A). Each of the input elements 234 may be configured to drive/actuate a different movement or action of the instrument 224. For example, a first input element 234a may control a first movement parameter (e.g., pitch, yaw, and/or roll about one or more axes) of one or more joints of the instrument 224 (e.g. wrist 227), while a second input element 234b controls a second movement parameter. Multiple input elements 234 may be configured to together drive/actuate a coordinated movement/actuation of the instrument 224 (e.g. pitch, yaw, opening or closing jaws, etc.) One or more of the input elements 234 may control an actuation of the end effector such as staple firing, clamp clamping, etc. In some embodiments, one or more of the drive elements 222 of the manipulator arm 202 are configured to be compatible with two or more of the input elements 234. In some embodiments, specific drive elements 222 or subsets of the drive elements 222 are compatible with only a single input element 234 or subset of input elements 234. For example, certain drive elements and input elements may be associated with high-load (e.g., high torque or force) applications, while other drive elements and input elements may only be configured for lower-load applications. In another example, certain drive elements and input elements may be associated with high-speed (e.g., high linear speed or high rotational speed) applications, while other drive elements and input elements may only be configured for lower-speed applications.

FIG. 2C is a schematic illustration of an example of drive assembly 250 configured in accordance with embodiments of the present technology. The drive assembly 250 includes a drive element 222 driven by one or more drivetrain subcomponents. For example, one of the drivetrain subcomponents can be an actuator 252. The actuator 252 can include, for example, a motor, a solenoid, or some other appropriate component configured to actuate the drive element 222. The drive assembly 250 can include one or more additional drivetrain subcomponents such as, for example, a transmission 254 configured to transmit driving force from the actuator 252 to the drive element 222. The transmission 254 can include one or more cables, pulleys, screws, pistons, and/or other components configured to transmit driving force to the drive element 222. As illustrated, the drive element 222 can interface with an input element 234. The interface between the drive element 222 and the input element 234 can be direct (e.g., via direct contact) or indirect (e.g., via use of one or more intermediate structures 256). Intermediate structures 256 can include, for example, adapters, sterile adapters, and/or other structures positioned physically between the drive elements and the input elements. The variable parameters of drive assembly 250 or instrument 224 can be sensed by any number of position, velocity, or acceleration sensors such as encoders, potentiometers, accelerometers, or other sensors to provide sensor data to the device 100 describing the movement of the instrument 224. Other sensors could include torque sensors, current sensors, voltage sensors, and/or temperature sensors. These sensors may be included in the drive assembly 250, the instrument 224, or elsewhere in the system. This sensor data may be used to determine motion of the objects manipulated by the drive elements 222, such as portions of the instrument 224.

As described in more detail in U.S. Pat. No. 6,331,181 (the entire disclosure of which is hereby incorporated by reference in its entirety), the instrument 224 will often include a memory 236, with the memory 236 typically being electrically coupled to a data interface (e.g. as part of the instrument interface 211). This data interface can allow data communication between memory 236 and a computer (e.g., the user control system 132, see FIG. 1A) when the instrument 224 is mounted on the manipulator arm 202 (FIG. 2A).

Instruments (e.g. instrument 104, 224) may differ in size, shape, number of joints, degrees of freedom, function, etc. For example, instruments may have different shaft diameters or end effectors. In some embodiments, the instruments are configured to be coupled to associated drive assemblies, removed from their associated drive assemblies, and be remounted to couple with the same drive assembly or another drive assembly, or be replaced with another instrument. This instrument coupling, removal, and remounting or replacement may occur during a procedure being performance by the medical device, or between procedures performed by the medical device. For a surgical example, a surgical stapler may be used in connection with a given manipulator arm 202 for a first procedure, or for a first portion of the first procedure. Another instrument can be installed on the manipulator arm 202 at another time (e.g. during another procedure or another portion of the first procedure). Additional details are provided in U.S. Pat. No. 8,823,308, the entire disclosure of which is hereby incorporated by reference in its entirety.

In some operational environments, instruments can be combined into combinations with multiple capabilities. Additional details related to these combinations are provided in U.S. Pat. No. 7,725,214 (disclosing "Minimally Invasive Surgical System"), the disclosure of which is incorporated herein by reference in its entirety. Details related to interfaces between the instruments and the manipulator assemblies are provided in U.S. Pat. No. 7,955,322 (disclosing "Wireless Communication in a Robotic Surgical System"), U.S. Pat. No. 8,666,544 (disclosing "Cooperative Minimally Invasive Telesurgical System"), and U.S. Pat. No. 8,529,582 (disclosing "Instrument Interfaces for Robotic Surgical Systems), the disclosures of which are all incorporated herein by reference in their entireties.

As described above, increased use of the components or subcomponents, of manipulator assemblies or instruments, as compared to that of other manipulator assemblies or instruments, can result in greater loading, use, or wear for those components or subcomponents. Certain embodiments of the present technology are configured to reduce such greater loading or wear. In various embodiments, use is allocated to the components (e.g., manipulator assemblies) or subcomponents (e.g., drive elements) in a random or pseudorandom manner, in a sequential order, based on historical data, or in a manner combining the foregoing. Examples of historical data include test data (e.g. performance test data), usage data (e.g. prior use history), and the like. Historical data associated with a plurality of drive elements can be data of a drive element, a subcomponent of the drive assembly coupled to any drive element of the plurality of drive elements (e.g. transmission elements, actuators, etc.), and/or other related structures involved in the physical operation of the drive element. As a specific example, usage or test data associated with of the plurality of drive elements can comprise usage or test data of a drive element, a subcomponent of the drive assembly coupled to any drive element of the plurality of drive elements, etc. These aspects are discussed in more detail here and further below.

As a specific example, certain embodiments of the present technology are configured to monitor specific loading, usage, or wear on the components and subcomponents of a device in order to estimate, empirically measure, or otherwise account for different types of loading, wear, or use on the components and subcomponents. Use/load monitoring can be performed manually, automatically, or with a combination of manual and automatic systems. Such systems and methods will now be described in a teleoperation context with respect to the medical device 100 illustrated in FIG. 1A. The techniques described in the teleoperation context can also be applied to non-teleoperated contexts and non-teleoperated components.

In this teleoperation example, for a given procedure, one or more specific instruments 104 are coupled to the one or more specific manipulator assemblies 102. These instruments may include medical instruments such as manipulation instruments (e.g., graspers, hooks, staplers, etc.) and imaging instruments (e.g., optical or infrared cameras, ultrasonic sensors, etc.), and/or other appropriate instruments for the given procedure. In systems that record couplings between instruments 104 and manipulator assemblies 102, the details of the coupling between the instruments 104 and the manipulator assemblies 102 (collectively, "teleoperated components") can be identified in any appropriate manner and recorded. For example, the operator O or other person can manually enter the couplings before or after the procedure. In some configurations, the manipulator assemblies 102 and/or the instruments 104 include structures configured to automatically identify the couplings between components. For example, either or both of the instruments 104 and manipulator assemblies 102 can include radio-frequency identification (RFID) tags, near-field communication (NFC) components, Bluetooth® beacons, embedded chips, optical UPC or QR codes, magnets providing unique magnetic signatures, or other components configured to identify and/or detect the type of instrument 104 coupled to a given manipulator assembly 102. The above-listed components can also be configured to help identify couplings between specific drive elements of the manipulator assemblies 102 with specific input elements of the instruments 104, as discussed in more detail below. The identified couplings of the teleoperated components can be recorded locally or in a remote database. For example, the control system 134 and/or the user control system 132 can include memory configured to receive and store identified couplings.

As discussed above, the identified couplings can include the specific pairings between individual drive elements of the manipulator assemblies 102 with types of input elements of the instruments 104. For example, a first drive element of a first manipulator assembly 102 may be coupled with a first input element of an instrument 104, and a second drive element of the first manipulator assembly 102 may be coupled with a second input element of a different type than the first input element.

The recorded data reflecting pairings between specific instruments 104 and specific manipulator assemblies 102 and/or pairings between specific drive elements and specific input elements) can be a subset of the overall historical data. The overall historical data can include the type of instrument 104 coupled to a manipulator assembly 102, the date and/or duration of use of the instrument 104 with the manipulator assembly 102, the installation position of the manipulator assembly 102, the pose of the manipulator assembly 102, the number and/or types of actuations of the specific drive elements (e.g., the degrees of freedom driven by the drive elements), the load or estimated wear borne by the drive assemblies comprising the drive elements, the operating conditions, any of the previously listed parameters affecting load, use, or wear, and/or other information associated with the couplings and uses of the teleoperated components. The number/types of actuation data associated with the drive elements can include number and/or frequency of direction reversals (e.g., rotations/translations of the drive elements in different directions), forces realized (e.g., aggregate and/or peak values), torques realized (e.g., aggregate and/or peak values), speed of movement realized, the degree of freedom associated with previously paired instruments/input elements, the identity of a user of the manipulator, and/or magnitude of overall motion. The above-described data can be recorded and associated with manipulator assemblies, or with drive elements or other parts of the drive assemblies. In some embodiments, environmental conditions are associated with the recorded historical data. These environmental conditions can include temperature, humidity, altitude, etc.

The recorded historical data can be compiled and/or processed by a server. The server can be local (e.g., associated with the control system 134, the user control system 132, and/or be on hardware or software component located at the facility in which the teleoperated components are located). In some configurations, the server is remote or otherwise offsite from the medical device 100. For example, the server can be part of a distributed network of servers (e.g., a "cloud" network) or part of backend hardware located at a manufacturer or service provider facility.

Various metrics or other proxies of historical loading, use, or wear can be calculated based on the recorded historical data and associated with the specific manipulator assemblies 102, drive elements, instruments 104, and/or input elements. In some configurations, a binary metric is used. For example, use of a high-load instrument (e.g., a surgical stapler) or use of a high-load input element garners a "1" while low-load instrument/input element pairings are recorded as a "0" value. Binary scoring could also be associated with the specific type of instrument 104 or input element. For example, a manipulator assembly 102 or drive element (or other part of the drive assembly comprising the drive element) can be given a "1" associated with a specific instrument 104 or input element each time the manipulator assembly 102 is paired and used with that instrument 104 input element, or that drive element is paired and used with that input element.

The metrics for historical loading, use, or wear can comprise, in some applications, be aggregations, summations, or other combinations of all or a subset of the above-recited historical data. For example, total actuations, total time spent in use (e.g., with a specific type of instrument or input element), total number of direction changes/reversals, or other operational parameter etc. can be associated with a given manipulator assembly 102 and/or with one or more of the drive elements (or with the drive assemblies comprising the drive elements). As a specific example, a metric can comprise a combination of the type of instrument 104 (or the input element) coupled with a manipulator assembly 102 (or coupled to a drive element), along with the total time of the coupling. As a further example, the linear or rotary forces experienced by the manipulator assembly 102 (or by the drive element or another part of the drive assembly) can also be used in the combination. As another example, in some configurations, the number of direction reversals experienced by the manipulator assemblies 102 (or by the drive elements (or of the drive assemblies comprising the drive elements) can also be used in the combination, such as in addition to or instead of the number of revolutions and/or translations. Additional operating parameters may be used to formulate aggregated metrics.

In some embodiments, the manipulator assemblies 102 or the drive elements (or other parts of the drive assemblies comprising the drive elements), can be tested for performance, or for specific wear. This testing could be performed onsite or at separate testing facility. The test data observed during such tests can be combined with the historical data and used as appropriate in determinations of metrics for loading, wear, use, etc. For example, the test data can supplement calculation of an overall aggregated metric for the specific manipulator assemblies 102, or for the drive elements. For example, an observed wear measurement of a transmission element can be used in determining an aggregated metric associated with the drive element coupled to the transmission element. In some applications, such observed wear is assigned a value between "1" and "N," with N being a number greater than one. For example, N could be 2. In this case, each manipulator assembly 102 or drive element thereof can be assigned a value between 1 (low or no observed wear) and 2 (high wear).

The empirical/observed loading, use, or wear can be associated with specific types of loading, use, or wear and used to supplement metrics that implicate those types of loading, use, or wear. For example, observed loading, use, or wear on certain gears or bearings may be associated with specific types of loading, use, or wear (e.g., number of direction reversals, magnitude of load, etc.). This specific observed loading, use, or wear can be assigned a value that is used in calculations of the actual metrics. For example, observed loading, use, or wear associated with a number of direction reversals can be added to, multiplied by, or otherwise combined with previously recorded metrics associated with direction reversals. Such associations can be made with respect to some or all of the other above-described quantified features.

The observed wear can be input to a user interface (UI) on one of the control systems (e.g., control systems 134, 132 in FIG. 1A). In some configurations, the observed wear can be input into another UI on, for example, a handheld device, a terminal in a location other than the room in which the medical device is located, or some other UI. For example, a test facility may include one or handheld or other terminals having UIs for inputting observed wear characteristics (e.g., visually observable wear) associated with specific teleoperated components and/or subcomponents of the teleoperated components. Data input into the above-described UIs can be sent via a wired connection, wireless connection, or other connection to the above-described server for storage and analysis. Data from tests (e.g., performance or wear tests) can be automatically compiled and sent to the above-described server. The data from the tests can be combined with other historical data to provide a more holistic metric for one or more component/subcomponent. In some configurations, data from wear tests instead of data from observed wear are compiled.

The above-described metrics and data can be associated with specific manipulator assemblies 102, drive elements (or other elements of the drive assemblies associated with the drive elements) over the life of that structure. For example, specific manipulator assemblies and specific drive elements (and/or other elements of the drive assemblies associated with the drive elements) can be assigned unique identifiers. In some embodiments, each drive element has an identifier unique to the structure that is attached to (e.g. to a specific manipulator assembly 102), but is not necessarily universally unique. The historical data and/or determined metrics can be associated with these unique identifiers, allowing a user to recall metrics for manipulator assemblies 102 and/or specific drive elements available for use with a given procedure.

Recorded usage data is a type of historical data and can be updated in response to additional data obtained in subsequent procedures just like other types of historical data can be updated (e.g. recorded test data can be augmented by additional test data). The historical data (e.g. usage data, test data, etc.) can be managed by a control system (e.g., the below-described management systems) or other automated system. Assignment recommendations for specific instrument-manipulator pairings, input element-drive element pairings, and/or other operating configurations can be generated by the control system. The control system can convey the recommendation to a user. In some embodiments, the historical data (usage data, test data, etc.) can be presented to a user as single values in multiple categories (e.g., total use with a certain type of instrument, total wear estimation for a single drive element, total time used, etc.). In some applications, the historical data (e.g. usage data, test data, etc.) can be presented as a table, graph, or other format indicating metric values and other data over the course of time. In some instances, the historical data (e.g. usage data, test data, etc.) of the manipulator assemblies and/or drive elements are retained after maintenance or repair. In other instances, such historical data is totally or partially erased or reset after maintenance or repair, such as based on the type and result of the maintenance or repair). In applications where historical data includes values over time, the erasure or resets may be noted in the history.

Figure 3:
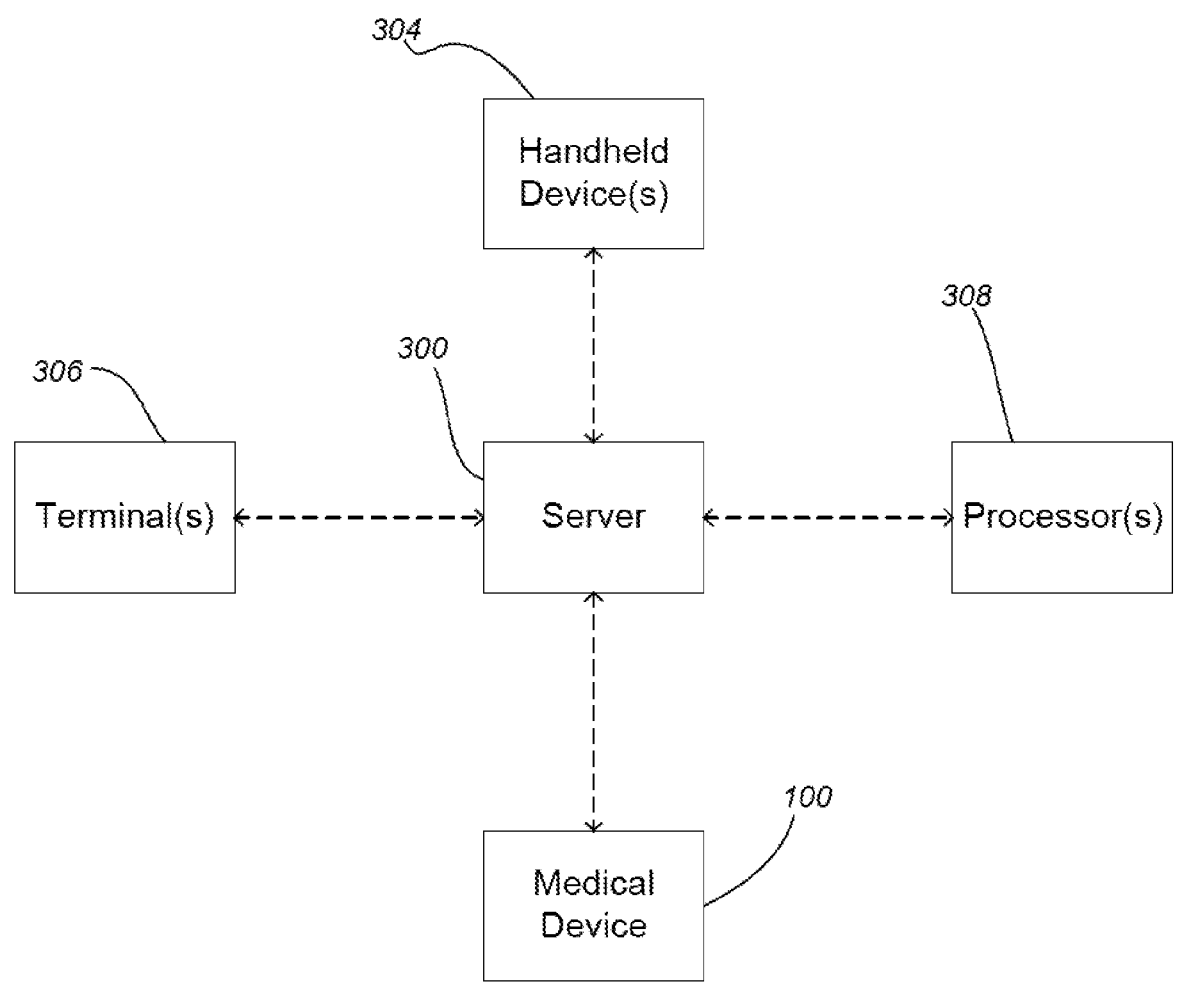
FIG. 3 is a schematic illustration of a system for managing devices in accordance with embodiments of the present technology.

As illustrated in FIG. 3, the historical data and associated data can be maintained and stored on a server 300. This server can be the same, above-described server. One of skill in the art will appreciate that specific hardware and software features may be added and/or omitted to accommodate the above-described collections and other functions. As indicated by the broken arrows, the server 300 can be operably connected to one or more other components or systems. The components can include the medical device 100, one or more handheld devices 304, one or more terminals 306, and/or one or more local (to the server) or remote processors 308 (collectively, data components). As described above, the server 300 may be local to or physically integral with any of the other data components. Data from each of the data components may be communicated over a wired connection, a wireless connection, and/or via cloud server. Each of the data components may be configured to access information from the server 300. Preferably, such access is limited to the data associated with specific manipulator assemblies 102 and drive elements owned or operated by the entity requesting information from the server 300.

Figure 4A:
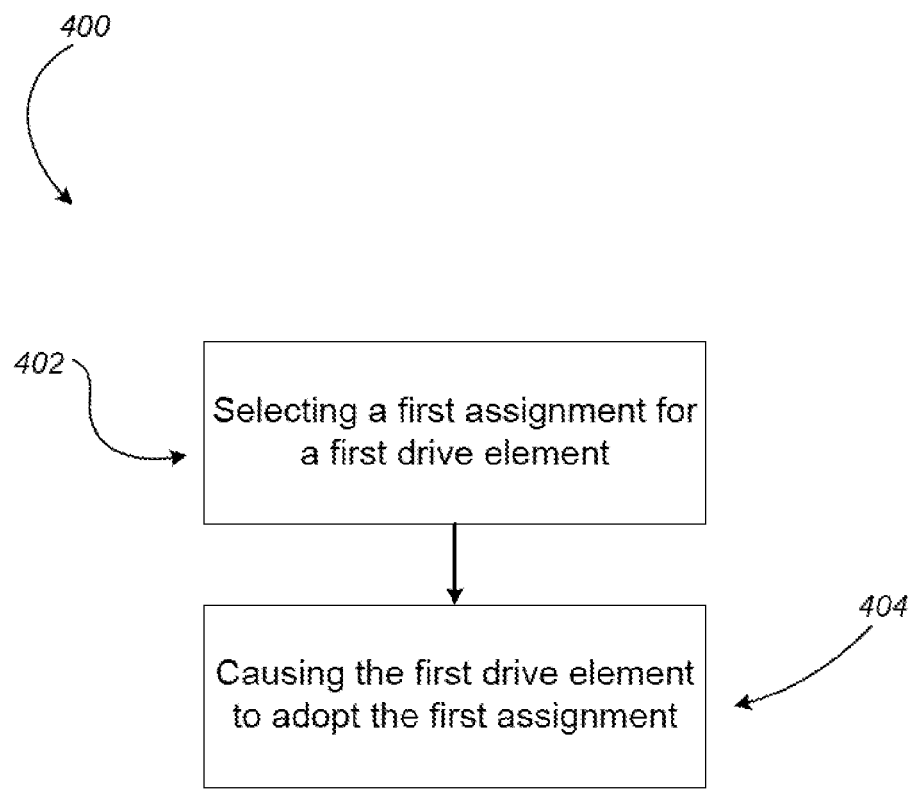
FIG. 4A is a schematic illustration of a method of selecting assignments for drive elements in a medical device configured in accordance with embodiments of the present technology.

FIG. 4A illustrates a method 400 of selecting assignments for specific drive elements of a device having a drive assembly configured to removably couple with an instrument in accordance with embodiments of the present technology. The method 400 can include, for example, selecting a first assignment (e.g., an assignment associated with a first pairing of a drive element of the device with a first input element of the instrument) for a first drive element of the drive assembly (block 402). This first assignment can be selected from a plurality of assignments available to at least two drive elements of a plurality of drive elements of the drive assembly. The method 400 can further include causing the first drive element to adopt the first assignment (block 404). The first assignment can be associated with a pairing of the first drive element with a first input element of a plurality of input elements of the instrument. In some embodiments, causing the first drive element to adopt the first assignment can include configuring one or both of the drive assembly and the instrument to pair the first drive element with the first input element.

Figure 4B:
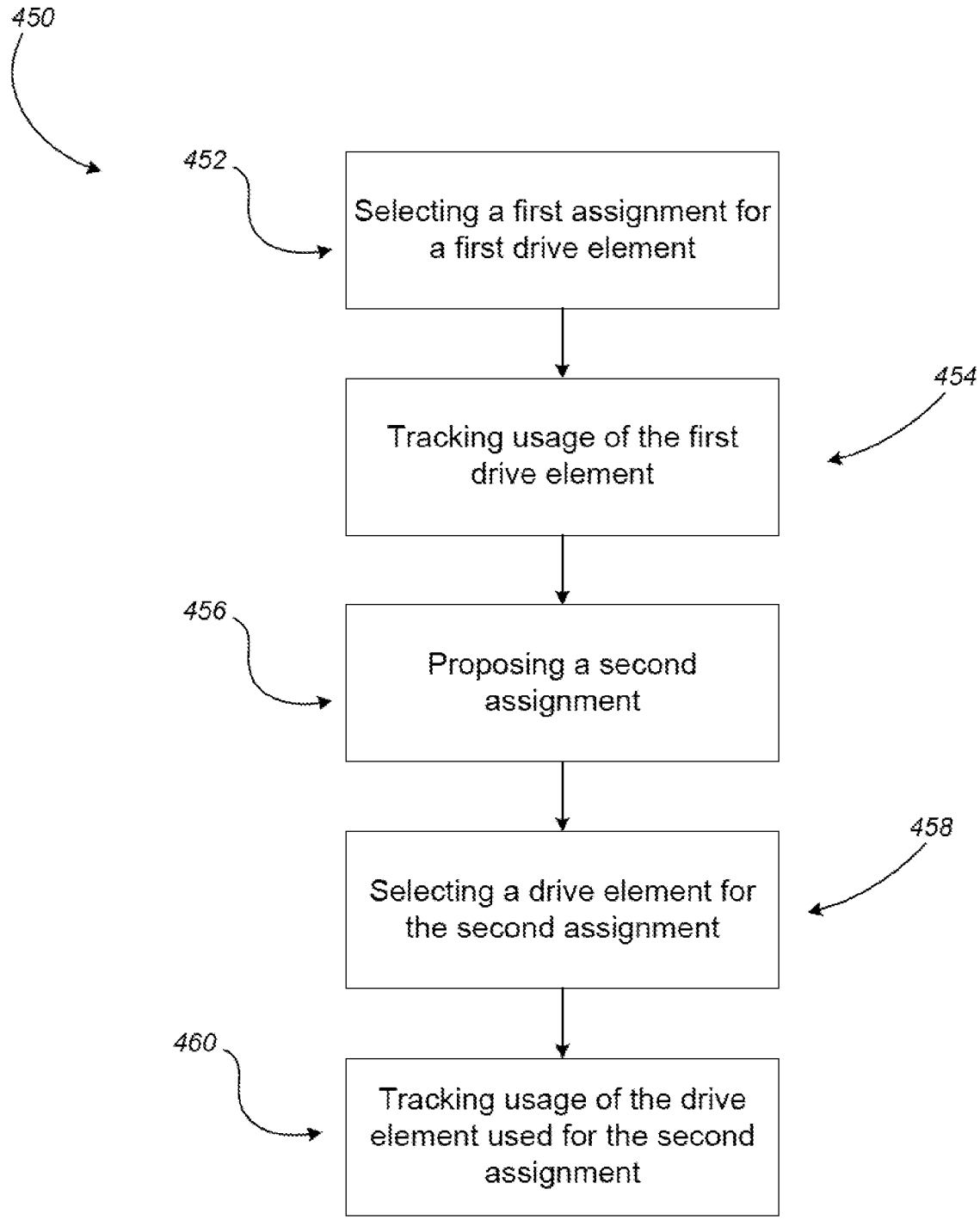
FIG. 4B is a schematic illustration of another method of selecting assignments for drive elements in a medical device configured in accordance with embodiments of the present technology.

FIG. 4B illustrates another method 450 of selecting assignments for specific drive elements of a medical device for a given proposed procedure in accordance with embodiments of the present technology. In some configurations, the selections described in connection with the method 450 of FIG. 4B are made in order to spread or balance loading, usage, or wear on drive elements or other components of a medical device. The method 450 can include an initial step or process similar to the method 400 described above. In particular, beginning at block 452, the method 450 includes selecting a first assignment (e.g., a first pairing of a drive element with a first input element) for a first drive element of a drive assembly. Selection of the first assignment can be conveyed to a user of the system via instructions (e.g., instructions for configuring/reconfiguring a drive assembly of the system or for installing/orienting an instrument in a particular manner). The first drive element can be, for example, one of the drive elements 222 of the drive assembly 220 of FIG. 2B. Similarly, the first input element can be one of the input elements 234 of the instrument 224 of FIG. 2B. Selection for the first drive element can be based, at least in part, on the suitability of functional characteristics of drive element for the first assignment as compared to other drive elements. For example, the first assignment may be associated with a high-load application for which only a subset of the drive elements is suitable or may be associated with a type of input element with which only a subset of the drive elements is configured to couple. In some embodiments, the first assignment may be associated with use in a type of procedure for which only a subset of the drive elements is usable. The requirements of the first assignment (e.g., the type of instrument, type of procedure, etc.) can be determined based on one or more of: a stage of a procedure; a number of uses of the plurality of drive elements; a previous instrument previously coupled with the drive assembly; a second instrument coupled with a second drive assembly of the medical device; previous instrument degrees of freedom driven by the plurality of drive elements; and an identity of the user of the device.

The first assignment can be available to two or more of the drive elements. In some embodiments, the first assignment is selected from a plurality of available assignments in a random or pseudorandom manner. In some embodiments, the first assignment is selected from a list of assignments arranged in sequential order. In some embodiments, the first assignment is selected based on historical data associated with the first drive element, such as based on previous use of the first drive element.

The use of the first drive element during the first assignment can be monitored, tracked, aggregated, and/or recorded (block 454). Tracked statistics can include, for example, number of uses of the drive elements, identification of the instrument driven by the drive elements, degrees of freedom driven by the drive elements, duration of use, loads realized during use, and/or any other useful information. The method can include proposing a second assignment (e.g., a pairing with an input element) for a drive element (block 456). A drive element can be selected for the second assignment (block 458) based on, for example, an evaluation of historical data of a plurality of drive elements. In some embodiments, historical data includes usage data and/or test data (e.g., performance test data). The historical data associated with a given drive element can include historical data of the drive element itself, historical data of a subcomponent of the drive assembly coupled to the drive element, such as a transmission element or an actuator associated with the drive element. In some configurations, the second assignment is assigned to a second drive element; where the second assignment is associated with a second input element, the second drive element can adopt the second assignment during a time overlapping with when the first drive element has adopted or is adopting the first assignment. In some embodiments, the second assignment is assigned to the first drive element, and the first drive element is transitioned from the first assignment to the second assignment.

The first and second assignments can be assigned to the first and second drive elements such that the less used of the two drive elements is paired with a more demanding input element of the input elements associated with the first and second assignment. The less used drive element can be the drive element with a lower amount of use as measured by a use metric (e.g. based on duration of use, magnitude of experienced forces, another parameter described above, etc.), and/or a lower wear amount, and/or other parameters. In some embodiments, the less used drive element is determined based on at least one of: a peak force experienced by the drive elements; a peak torque experienced by the drive elements; an aggregate force experienced by the drive elements; a degree of freedom driven by the drive elements; a frequency of actuation experienced by the first drive element; a magnitude of motion experienced by the first drive element; a number of direction reversals experienced by the first drive element; a speed of movement experienced by the first drive element; and an aggregate torque experienced by the drive elements. In some embodiments, the method can include tracking usage of the drive element used in the second assignment (block 460) and recording the usage data as historical data.

Figure 5A:
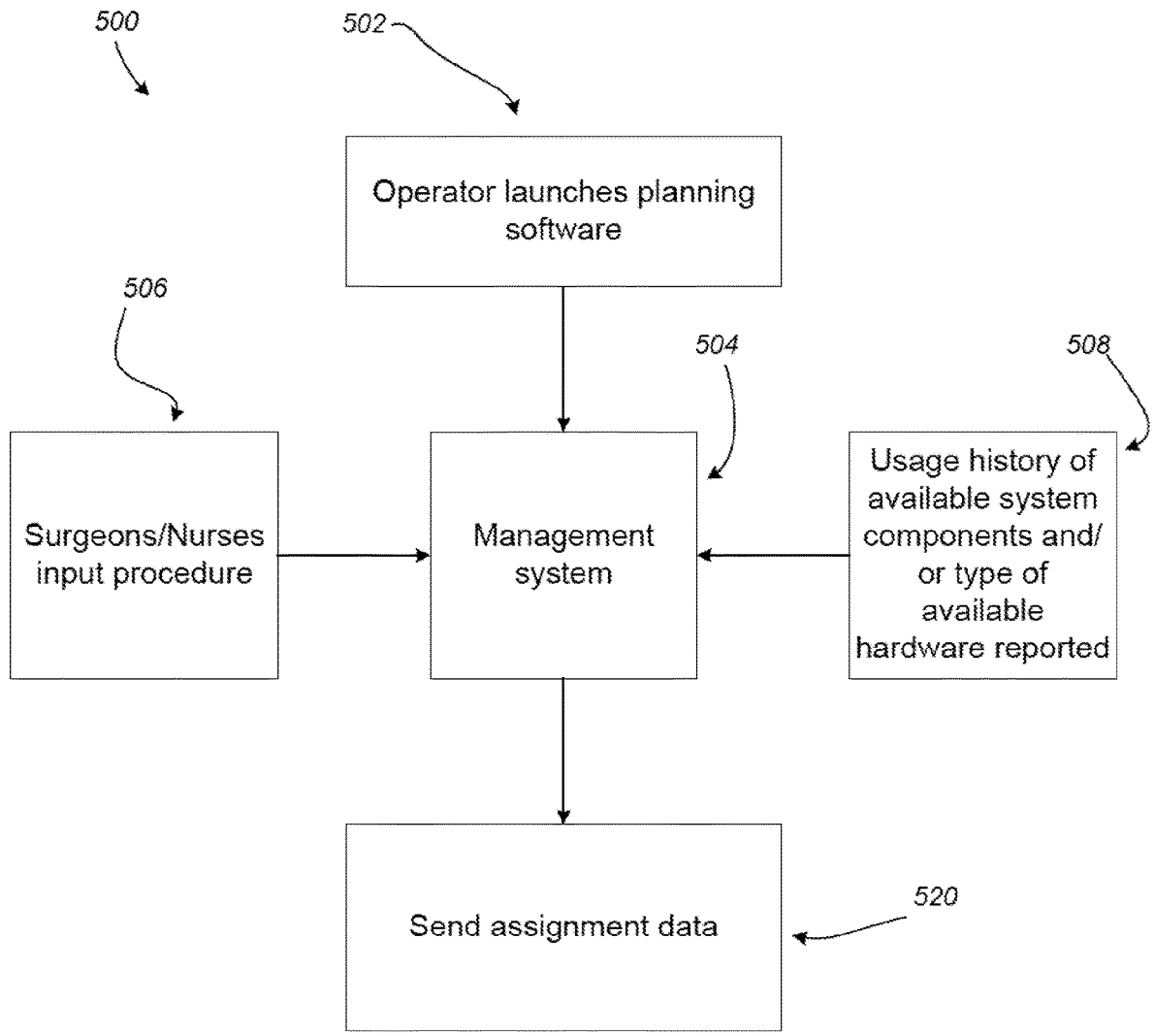
FIG. 5A is a schematic illustration of a method of managing devices in accordance with embodiments of the present technology.
Figure 5B:
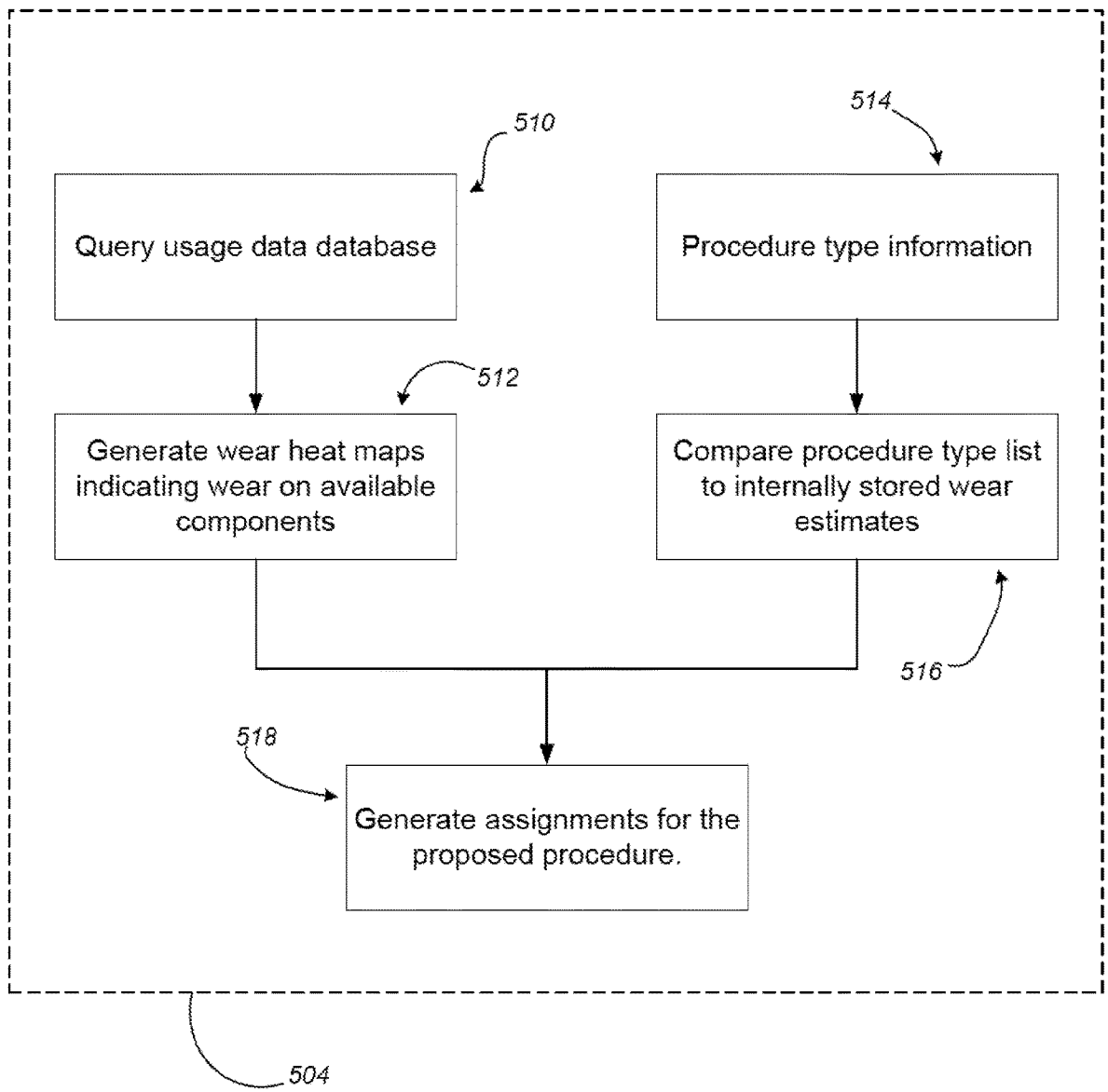
FIG. 5B is a schematic illustration of additional method steps of the method of FIG. 5A.

FIGS. 5A and 5B illustrate an example method 500 of managing devices in accordance with embodiments of the present technology. The method 500 can be used for balancing or spreading the loading, use, or wear for teleoperated components and/or subcomponents. As illustrated at block 502, for a given procedure, an operator can launch planning software associated with setting up a medical device for a given procedure. A management system 504 may be notified of the software launch. The management system 504 can be, for example, a control system having at least one processor and a memory. The management system 504 can include instructions configured to cause the at least one processor to perform various below-described operations. The management system 504 can be maintained, for example, on the above described-server 300 or some other data-processing hub configured to manage data and instructions associated with spreading wear on the medical device. The management system 504 may be maintained and/or operated local to the medical device (e.g., in the same room or at the same facility). In some embodiments, the management system 504 is maintained and/or operated at a location remote to the medical device.

At block 506, an operator can input (e.g., via one of the above-described UIs) the upcoming procedure. For a medical example, a type of surgery or other procedure may be input. In some applications, the required instruments and/or estimated time of use of specific instruments may be input. For example, the estimated time of use can be based at least in part on observed times of use in previous procedures of the same type. This information may be conveyed to the management system 504. In some configurations, a scheduling system (e.g., a hospital's scheduling system) can automatically input information about upcoming procedures.

Referring to block 508, the usage histories of the various available teleoperated components (e.g., manipulator assembly 102, manipulator arm 202 and/or drive elements 222 in FIGS. 1A and 2B) may be reported to the management system 504. In some embodiments, the available overall system architecture (e.g., mounting structures, type of surgical table, etc.) may also be reported. The usage histories may be reported from the above-described server 300 or from some other local or remote database.

Further details of the functions performed by the management system 504 are explained with reference to FIG. 5B. As indicated in block 510, the management system 504 can, in some configurations, query the usage history information (e.g., the information provided in block 508 of FIG. 5A) to generate a heat map (block 512) indicating wear on the available teleoperated components. This heat map can indicate the above-described usage metrics and usage histories of various available teleoperated components. For example, aggregated totals from previous binary metrics could be reflected for each teleoperated component and/or subcomponent could be reflected in a heat map of the available inventory.

Before, after, or contemporaneous with performing the operations in blocks 510 and 512, the procedure type information can be analyzed (block 514). The procedure type information can include the required instruments, manipulator poses, usage durations, and other procedure-specific information. In some embodiments, the procedure type information is pulled from a database. In some embodiments, the surgeon, nurse, or other person, inputs the procedure type information (e.g., as indicated in block 506 of FIG. 5A). The functions performed by the management system can include comparing the input procedure type wear estimates associated with the procedure (block 516). The wear estimates can be calculated using usage information associated with the type of procedure (e.g., the type of instruments, durations of use, and other information). Wear estimates associated with various procedures may be manually calculated. In some embodiment wear estimates are generated based on empirical data from past similar or identical procedures. For example, for a gall bladder removal, wear estimates may be generated based on previously performed gall bladder removal procedures, and the actual recorded data gathered from these past procedures. Wear estimates may be updated and stored on a server operated by a care provider (e.g., a hospital, hospital network, or other care provider) and/or on a server maintained by a manufacturer or other service provider separate from the care provider.

Given the data gathered and analyzed in blocks 510-516, the management system can generate assignments for the proposed procedure (block 518). The assignments can include which manipulator assemblies are to be used with which instruments and/or which drive elements should be used with which input elements. For some applications, including those using the rotatable architectures described below with respect to FIGS. 6A and 6B, proposed rotational alignment of the drive elements and/or input elements may be included in the assignment. Determining the appropriate assignments can include comparing different manipulator assemblies and/or individual drive elements and their respective usage histories, recorded data, observed data, and/or other metrics. In some instances, a "less used" manipulator assembly or drive element can be selected from the available inventory. The less used manipulator assembly or drive element can be the one that is (1) overall appropriate for the proposed procedure (e.g., it is high-load if high-load operations are required) and has (2) an overall aggregated metric or usage history for the proposed procedure that indicates that has been used less for the procedure than some or all of the other available manipulator assemblies and/or drive elements. The scores/usage history can be queried with respect to overall aggregate metric value or by a metric value in specific subcategories (e.g., types of wear). Determining and assigning a less used component can help to distribute wear more evenly through the inventory of a given care provider to prolong the overall life of the manipulator assemblies.

In some implementations, the management system 504 can be configured to assign manipulator assemblies and/or drive elements based on a predetermined schedule over the course of multiple assignments. For example, the manipulator assemblies/drive elements may be assigned a schedule that is arranged to spread or balance usage, load, and/or wear on that manipulator assembly and/or drive element as the manipulator assembly and/or drive element is reused in subsequent assignments. The schedule can include an order in which types of instruments should be used with a specific manipulator assembly or the types of input elements that should be used with a specific drive element. Following predetermined schedules in this matter can help to ensure that each manipulator assembly and drive element is worn more evenly that would be the case without a schedule.

In implementations in which the wear on individual drive elements is managed, the above-described assignments can be analyzed and determined taking into account the orientation and positioning of multiple drive elements on each manipulator assembly. For example, scenarios may occur wherein a first drive element on a manipulator assembly is scheduled for use with an input element on a certain instrument in the proposed procedure and/or the first drive element is a less used drive element for the proposed procedure. A second drive element on that same manipulator assembly may not be schedule for use with another input element of the same instrument in the proposed procedure or may not be a less used drive element for the proposed procedure. In such scenarios, overall suitability of a manipulator assembly for a specific assignment can account for the respective suitability of its individual drive elements. These suitability measures (e.g., status as less used or conformance with a predetermined schedule) can be weighed and/or averaged to determine the overall suitability of the manipulator assembly for a given assignment compared to other manipulator assemblies.

These recommended assignments can be communicated (block 520—also illustrated in FIG. 5A) via a software interface or other suitable interface. For example, the interface could comprise a mechanical constraint that impedes or prohibits the operator from connecting an instrument to a manipulator assembly in any orientation or position other than a specific assigned orientation or position (e.g., an orientation that matches individual drive elements with individual input elements in a desired arrangement). In some embodiments, the interface could comprise a sensor that provides an indication of instrument orientation or position, and the system can provide an indication (e.g., audible, visible, and/or tactile feedback such as alarm message, sound, or vibrations) configured to alert a user if an instrument is not oriented or positioned in a manner consistent with the assignment. In some embodiments, the assignments are communicated to an operator. The communication can occur prior to a procedure, during a break in a procedure, and/or between a first procedure and a second procedure. In some embodiments (e.g., those illustrated in FIGS. 6A and 6B), the management system can send a signal to a manipulator assembly or instrument to rotate their respective rotatable substrate to align the drive/input elements in the assigned configuration. The recommended assignments can include assignments to use specific manipulators/drive elements with specific instruments/input elements for only part of the proposed procedure, and then switching the assignments during the procedure. In practice, assignment recommendations for specific drive elements with specific input elements can include recommended installation orientations of the instrument with respect to the manipulator assembly. Instructions to modify the drive element-input element assignment can include, for example, instructions to rotate the instrument with respect to the manipulator assembly. In instances where a software interface is used, the software interface local to the operator (e.g., robotics user) may receive information from the management system and convey the recommended assignments to the operator.

Figure 6A:
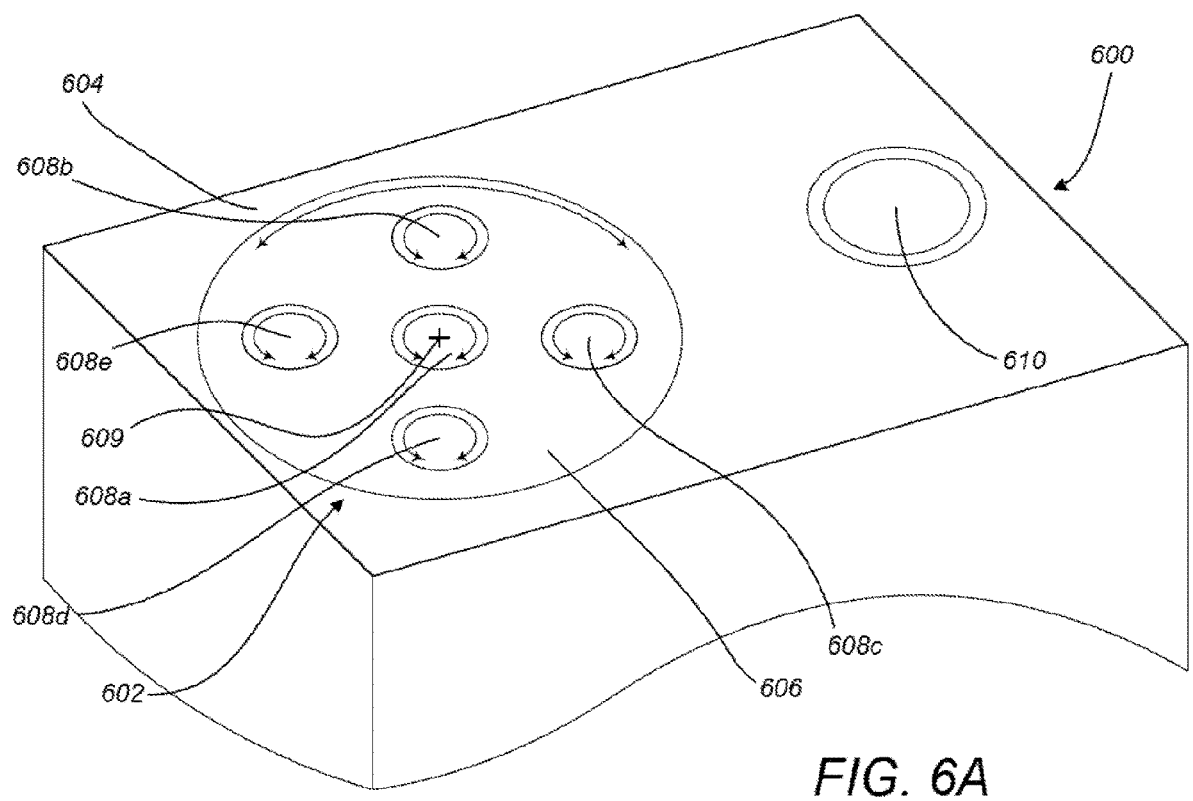
FIG. 6A is a perspective schematic illustration of a drive assembly configured in accordance with an embodiment of the present technology and having a rotatable substrate mounted to a fixed substrate.
Figure 6B:
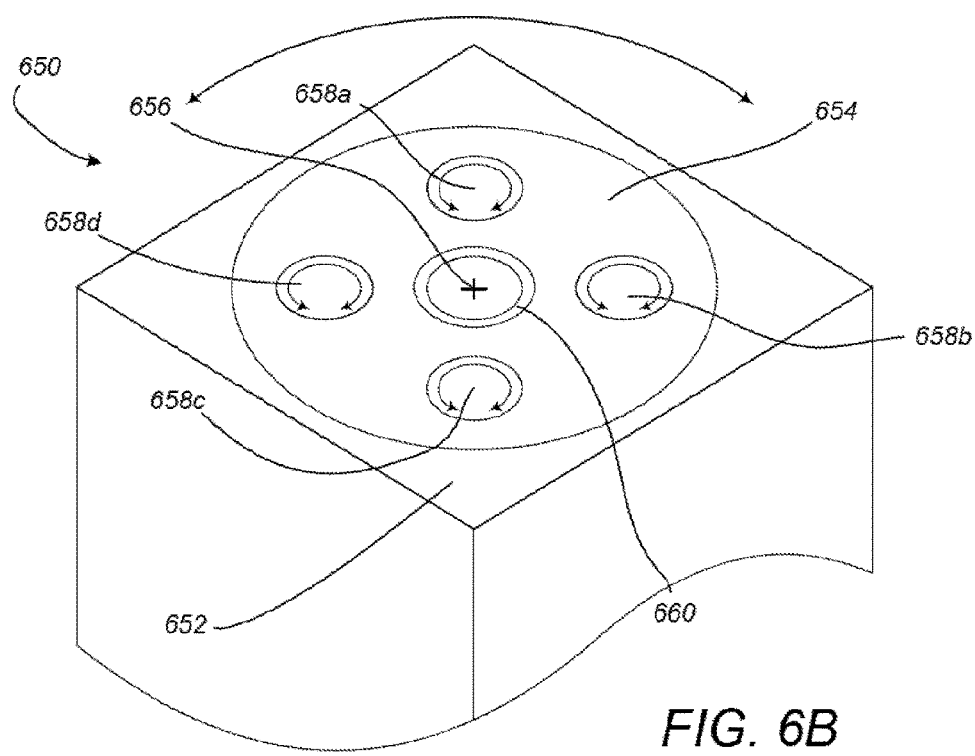
FIG. 6B is a perspective schematic illustration of a drive assembly configured in accordance with an embodiment of the present technology.

FIGS. 6A and 6B illustrate example input element and/or drive element arrangements that may be used to modify the interface between an instrument and a drive assembly of a device (e.g. such as a drive assembly disposed on a manipulator assembly of a medical device). Each of the arrangements in FIGS. 6A and 6B are described as interface arrangements, as the distribution and function of the components can be implemented on one or both of the instrument and the manipulator. The illustrated and described interface arrangements may, in some embodiments, be configured to transition between a first configuration wherein a first drive/input element of a plurality of drive/input elements is positioned to couple with a first input/drive element of the plurality of input/drive elements, and a second configuration, wherein the first drive/input element of the plurality of drive/input elements is positioned to couple with a second input/drive element of the plurality of input/drive elements.

FIG. 6A, for example, illustrates a first interface arrangement 600 having a second subcomponent 602 that is rotatable relative to a first subcomponent 604. The second subcomponent 602 can comprise, for example, a substrate 606 rotatably mounted to the first subcomponent 604. The first subcomponent 604 can comprise, for example, a part of a chassis or a housing of an instrument, or of a drive assembly of the device (e.g. a part of a link, or other portion of a manipulator assembly of a medical device). While the substrate 606 is illustrated as having a generally circular cross section, and first subcomponent 604 is illustrated as having a generally rectangular cross section, other cross-sectional shapes are also possible.

The substrate 606 can support one or more interface elements 608a-e (collectively, "608"). As used herein, "interface elements" refer to either drive elements if implemented on a drive assembly, or input elements if implemented on an instrument. The interface elements 608 can be rotary elements (e.g., discs are shown, and other shapes may be used), linear elements (e.g., tabs, nuts, etc.), or some combination thereof. Other element types of different shapes, sizes, and motion are also considered. In the example shown in FIG. 6B, the interface elements 608 are arranged in a rotationally symmetrical arrangement about an axis of rotation 609 of the substrate 606. Rotation of the second subcomponent 602 relative to the first subcomponent 604 locates the interface elements 608 in different rotational positions relative to the first subcomponent 604. In some embodiments, an interface element (e.g., the first interface element 608a in FIG. 6A) is positioned along the axis of rotation 609 of the rotatable substrate 606.

A shaft 610 can extend from the first subcomponent 604 (For an instrument, this may be in a manner similar to that of the shaft 232 illustrated in FIG. 2B.) The shaft 610 can be laterally spaced (e.g., in a direction normal or oblique to the length of the shaft 610) from the rotatable substrate 606. In some embodiments, the shaft 610 extends from the substrate 606. The shaft 610 can be coupled to an end effector (not shown) on an end of the shaft 610 opposite the substrate 606.

FIG. 6B, for example, illustrates an embodiment of a second interface arrangement 650. The second interface arrangement 650 includes a first subcomponent 652 and a second subcomponent 654 mounted to the first subcomponent 652. The second subcomponent 654 can be rotatably or fixedly connected to the first subcomponent 652. As such, either the second subcomponent 654 or the entire second interface arrangement 650 can be rotated, as indicated by the broken arrows in FIG. 6B, to allow for a plurality of rotational locations of the interface elements 658a-d (collectively, "658"). In the example shown in FIG. 6B, the second interface arrangement 650, including the subcomponents 652, 654, are rotationally symmetric about a central axis 656 (e.g., an axis extending normal to the page of FIG. 6B) of the second interface arrangement 650. The second subcomponent 654 can include a plurality of interface elements 658 and a shaft 660. In some embodiments, an interface element is coaxial with the central axis 656. In some embodiments, the shaft 660 is coaxial with the central axis 656 of the second subcomponent 654. In some embodiments, the interface elements 658 are mounted directly to the first subcomponent 652 without the use of a second subcomponent 654.

Accordingly, rotation of the second subcomponent 602, 654 of the interface arrangements 600, 650 allow the interface arrangement 600, 650 to couple with another interface arrangement with the respective interface elements 608, 658, in a plurality of different positions relative to their respective base components (e.g. first subcomponent 604, 652)

While certain numbers of interface elements 608, 658 are illustrated with respect to first and second interface arrangements 600, 650, other numbers of interface elements may be used with respect to each of the first and second interface arrangements 600, 650. Example other numbers of interface elements include two, three, or more interface elements.

In use, coupling between the interface elements 608, 658 and the other interface elements with which they are coupled (e.g., complementary input elements of instruments or drive elements of drive assemblies) can be randomized or pseudorandomized. As used herein, "pseudorandom," "pseudo-randomly," "pseudorandomized," and similar word variants refer to arrangements that are randomized according to one or more structured rules. For example, some interface elements 608, 658 may be structurally and/or functionally incompatible with certain drive elements or input elements, and thus a pseudorandom arrangement would account for this limitation while otherwise randomizing the couplings between interface elements 608, 658 and their corresponding mating elements.

The randomness of the coupling between the interface elements 608, 658 and corresponding input or drive elements can be implemented in several ways, some of which are described herein. For example, an operator of a medical device can be directed to randomly rotate the rotatable substrates (e.g., substrate 606 and subcomponent 654 in the illustrated embodiments of FIGS. 6A and 6B) before coupling the interfaces of components to each other. Such directions can include confirming that high-load interface elements are paired with high-load drive/input elements to manage the loading, usage, or wear.

In some embodiments, the components having either a first interface arrangement 600 or second interface arrangement 650 can be structured and configured to automatically rotate their respective rotatable substrates. For example, such components can include a motor or other structure configured to rotate the rotatable substrates in response to a manual actuation (e.g., pressing of a button, turning of a knob, etc.) and/or in response to a control signal from a local or remote controller. The degree of rotation of the rotatable substrates can be selected from a subset of options so that the interface elements are in positions appropriate for coupling with matching elements. These options can include incremental rotations associated with the number of interface elements on the substrate. For example, degrees of rotation associated with substrates having four circumferentially distributed interface elements (as illustrated in FIGS. 6A and 6B) can be measured in 90° increments (+90°, +180°, +270°, and in some embodiments 0° for no rotation). The controller or other mechanism assigned to determine the degree of rotation can be configured to randomly or pseudo-randomly select from the subset of rotational options. Randomizing or pseudo-randomizing the rotational alignment between the components of the medical device can, in the aggregate, more evenly distribute the loading, use, or wear of various subcomponents over the course of several procedures, operations, or other uses.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Moreover, the various embodiments described herein may also be combined to provide further embodiments. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment.

For ease of reference, identical reference numbers are used to identify similar or analogous components or features throughout this disclosure, but the use of the same reference number does not imply that the features should be construed to be identical. Indeed, in many examples described herein, identically numbered features have a plurality of embodiments that are distinct in structure and/or function from each other. Furthermore, the same shading may be used to indicate materials in cross section that can be compositionally similar, but the use of the same shading does not imply that the materials should be construed to be identical unless specifically noted herein.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms may also include the plural or singular term, respectively. As used herein, with respect to measurements, terms of degree such as "about," "approximately," "substantially," etc. mean +/−5%. Additionally, the term "comprising" is used throughout to mean including at least the recited feature(s) such that any greater number of the same feature and/or additional types of other features are not precluded. Directional terms, such as "upper," "lower," "front," "back," "vertical," and "horizontal," may be used herein to express and clarify the relationship between various elements. It should be understood that such terms do not denote absolute orientation. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A device management system comprising:
    a device comprising a drive assembly, wherein the drive assembly is configured to removably and physically couple with an instrument when the instrument is mounted to the device, and wherein the drive assembly comprises a plurality of drive elements configured to cause movement of the instrument by driving a plurality of input elements of the instrument; and
    a control system comprising one or more processors and a memory, the memory comprising programmed instructions adapted to cause the one or more processors to perform operations comprising:
        selecting, for a first drive element of the plurality of drive elements, a first assignment from a plurality of assignments, the first assignment being available to at least two drive elements of the plurality of drive elements, wherein the first assignment is associated with a first pairing of the first drive element with a first input element of the plurality of input elements; and
        causing the first drive element to adopt the first assignment.

2. The management system of claim 1, wherein selecting the first assignment comprises:
    selecting the first assignment from the plurality of assignments in a random or pseudorandom manner.

3. The management system of claim 1, wherein the first drive element has a present assignment, wherein assignments of the plurality of assignments are arranged in a sequential order, and wherein selecting the first assignment comprises:
    selecting a next assignment as the first assignment, wherein the next assignment follows the present assignment in the sequential order.

4. The management system of claim 1, wherein the operations further comprise obtaining historical data associated with the plurality of drive elements, wherein selecting the first assignment comprises determining the first assignment based on at least the historical data.

5. The management system of claim 4, wherein the operations further comprise:
    selecting, based on the historical data, a second assignment from the plurality of assignments for a second drive element of the plurality of drive elements; and
    causing the second drive element to adopt the second assignment during a time overlapping with when the first drive element has adopted the first assignment.

6. The management system of claim 4, wherein the historical data comprises usage data associated with the plurality of drive elements.

7. The management system of claim 6, wherein determining the first assignment based on at least the usage data comprises determining an amount of previous use of the first drive element.

8. The management system of claim 6, wherein the operations further comprise:
  tracking further usage information of the plurality of drive elements after the first drive element has adopted the first assignment and the instrument has been coupled with the drive assembly;
  selecting, for the first drive element of the plurality of drive elements, a second assignment from the plurality of assignments based on the further usage information; and
  causing the first drive element to transition from the first assignment to the second assignment.

9. The management system of claim 6, wherein the operations further comprise:
  determining, based on the usage data, a second assignment of a second drive element of the plurality of drive elements, the second assignment associated with a second pairing of the second drive element with a second input element of the plurality of input elements, such that a less used drive element of the first and second drive elements is paired with a more demanding input element of the first and second input elements.

10. The management system of claim 9, wherein the operations further comprise identifying the less used drive element, wherein identifying the less used drive element comprises determining at least one parameter selected from the group consisting of:
  a duration of use of the first drive element;
  a wear amount associated with the first drive element;
  a peak force experienced by the first drive element;
  a peak torque experienced by the first drive element;
  an aggregate force experienced by the first drive element;
  an aggregate torque experienced by the first drive element; and
  a degree of freedom corresponding to an input element previously driven by the first drive element;
  a frequency of actuation experienced by the first drive element;
  a magnitude of motion experienced by the first drive element;
  a number of direction reversals experienced by the first drive element; and
  a speed of movement experienced by the first drive element.

11. The management system of claim 6, wherein the usage data associated with the plurality of drive elements comprise usage data associated with at least one drivetrain subcomponent configured to drive at least one drive element of the plurality of drive elements.

12. The management system of claim 4, wherein the historical data comprises performance test data associated with the plurality of drive elements.

13. The management system of claim 1, wherein selecting the first assignment comprises determining the first assignment based on a type of the instrument.

14. The management system of claim 13, wherein the operations further comprise determining the type of the instrument based on:
  a procedure to be performed by the device; or
  a stage of the procedure being performed by the device; or
  a previous instrument previously coupled with the drive assembly; or
  a second instrument coupled with a second drive assembly of the device; or
  an identity of a user of the device.

15. The management system of claim 1, wherein causing the first drive element to adopt the first assignment comprises providing an instruction to a user of the device management system to:
  reconfigure the drive assembly, or
  install the instrument in a manner corresponding to the first assignment.

16. The management system of claim 1, wherein causing the first drive element to adopt the first assignment comprises causing the device to reconfigure the drive assembly.

17. The management system of claim 1, wherein causing the first drive element to adopt the first assignment comprises directing a rotational orientation of the drive assembly or of the instrument.

18. The management system of claim 1, wherein:
  the device comprises a robotic manipulator arm, the robotic manipulator arm comprising the drive assembly and a plurality of joints interconnecting a plurality of links;
  the device management system further comprises an input device configured to be manipulated by a user; and
  the operations further comprise:
    receiving a commanded motion from the input device, and
    commanding the robotic manipulator arm to move the plurality of joints and the plurality of drive elements to move the instrument in accordance with the commanded motion.

19. A method of operating a device comprising a drive assembly configured to removably and physically couple with an instrument when the instrument is mounted to the device, the method comprising:
  selecting, for a first drive element of a plurality of drive elements of the drive assembly, a first assignment from a plurality of assignments, the first assignment being available to at least two drive elements of the plurality of drive elements; and
  causing the first drive element to adopt the first assignment;
  wherein the first assignment is associated with a pairing of the first drive element with a first input element of a plurality of input elements of the instrument.

20. The method of claim 19, further comprising selecting the first assignment from the plurality of assignments in a random or pseudorandom manner.

21. The method of claim 19, wherein the first drive element has a present assignment, wherein assignments of the plurality of assignments are arranged in a sequential order, and wherein selecting the first assignment comprises:
  selecting a next assignment as the first assignment, wherein the next assignment follows the present assignment in the sequential order.

22. The method of claim 19, further comprising obtaining historical data associated with the plurality of drive elements, wherein selecting the first assignment comprises determining the first assignment based on at least the historical data.

23. The method of claim 22, wherein the historical data comprises usage data associated with the plurality of drive elements.

24. The method of claim 23, further comprising:
  determining, based on the usage data, a second assignment of a second drive element of the plurality of drive elements, the second assignment associated with a second pairing of the second drive element with a second input element of the plurality of input elements such that a less used drive element of the first and second drive elements is paired with a more demanding input element of the first and second input elements.

25. The method of claim 22, wherein the historical data comprises performance test data associated with the plurality of drive elements.

26. A non-transitory machine-readable medium or media comprising instructions that, when executed by one or more processors of a device comprising a drive assembly configured to removably and physically couple with an instrument when the instrument is mounted to the device, causes the one or more processors to perform a method comprising:
   selecting, for a first drive element of a plurality of drive elements of the drive assembly, a first assignment from a plurality of assignments, the first assignment being available to at least two drive elements of the plurality of drive elements; and
   causing the first drive element to adopt the first assignment;
   wherein the first assignment is associated with a pairing of the first drive element with a first input element of a plurality of input elements of the instrument.

27. The non-transitory machine-readable medium or media of claim 26, wherein:
   selecting the first assignment comprises selecting the first assignment from the plurality of assignments in a random or pseudorandom manner; or
   selecting the first assignment comprises selecting the first assignment from the plurality of assignments based on a sequential order of the plurality of assignments.

28. The non-transitory machine-readable medium or media of claim 26, wherein:
   the method further comprises obtaining historical data associated with the plurality of drive elements; and
   selecting the first assignment comprises determining the first assignment based on at least the historical data.

29. The non-transitory machine-readable medium or media of claim 28, wherein the historical data comprises: usage data associated with the plurality of drive elements or performance test data associated with the plurality of drive elements.

* * * * *